US009312097B2

(12) United States Patent
Nackashi et al.

(10) Patent No.: US 9,312,097 B2
(45) Date of Patent: Apr. 12, 2016

(54) SPECIMEN HOLDER USED FOR MOUNTING SAMPLES IN ELECTRON MICROSCOPES

(71) Applicant: PROTOCHIPS, INC., Raleigh, NC (US)

(72) Inventors: David P. Nackashi, Raleigh, NC (US); John Damiano, Jr., Apex, NC (US); Stephen E. Mick, Weimar, TX (US); Thomas G. Schmelzer, Cranberry Township, PA (US); Michael Zapata, III, Cary, NC (US)

(73) Assignee: PROTOCHIPS, INC., Morrisville, NC (US)

( * ) Notice: Subject to any disclaimer, the term of this patent is extended or adjusted under 35 U.S.C. 154(b) by 0 days.

(21) Appl. No.: 14/513,969

(22) Filed: Oct. 14, 2014

(65) Prior Publication Data

US 2015/0129778 A1    May 14, 2015

Related U.S. Application Data

(60) Continuation-in-part of application No. 13/799,871, filed on Mar. 13, 2013, now Pat. No. 8,859,991, which is a division of application No. 12/933,213, filed as application No. PCT/US2009/037396 on Mar. 17, (Continued)

(51) Int. Cl.
  *G21K 5/08*   (2006.01)
  *H01J 37/20*  (2006.01)
  *G01N 1/28*   (2006.01)

(52) U.S. Cl.
  CPC . *H01J 37/20* (2013.01); *G01N 1/28* (2013.01); *H01J 2237/202* (2013.01); *H01J 2237/2002* (2013.01); *H01J 2237/2007* (2013.01); *H01J 2237/2008* (2013.01); *H01J 2237/26* (2013.01)

(58) Field of Classification Search
  None
  See application file for complete search history.

(56) References Cited

U.S. PATENT DOCUMENTS

| 4,620,776 | A | * | 11/1986 | Ima | G02B 21/26 359/391 |
| 4,672,797 | A | * | 6/1987 | Hagler | G01N 1/28 250/440.11 |
| 4,833,330 | A | * | 5/1989 | Swann | H01J 37/02 250/442.11 |
| 4,996,433 | A | * | 2/1991 | Jones | H01J 37/20 250/442.11 |
| 5,089,708 | A | * | 2/1992 | Asselbergs | H01J 37/20 250/310 |
| 5,096,550 | A | * | 3/1992 | Mayer | C25F 3/02 204/212 |
| 5,124,645 | A | * | 6/1992 | Rhoden | G01R 1/0416 250/442.11 |
| 5,225,683 | A | * | 7/1993 | Suzuki | H01J 37/20 250/442.11 |

(Continued)

FOREIGN PATENT DOCUMENTS

| DE | 19533216 A1 | * | 3/1997 | ............ H01J 37/20 |
| DE | 19533216 C2 | * | 1/1998 | ............ H01J 37/20 |

(Continued)

OTHER PUBLICATIONS

Japanese Office Action and English Translation, Sep. 2, 2013.

(Continued)

*Primary Examiner* — Andrew Smyth
(74) *Attorney, Agent, or Firm* — Tristan A. Fuierer; Moore & Van Allen, PLLC

(57) ABSTRACT

A novel specimen holder for specimen support devices for insertion in electron microscopes. The novel specimen holder of the invention provides mechanical support for specimen support devices and as well as electrical contacts to the specimens or specimen support devices.

19 Claims, 19 Drawing Sheets

Related U.S. Application Data 2009, now Pat. No. 8,513,621, application No. 14/513,969, which is a continuation-in-part of application No. 12/599,339, filed as application No. PCT/US2008/063200 on May 9, 2008, now Pat. No. 8,872,129.

(60) Provisional application No. 61/037,115, filed on Mar. 17, 2008, provisional application No. 61/085,650, filed on Aug. 1, 2008, provisional application No. 60/916,916, filed on May 9, 2007, provisional application No. 60/974,384, filed on Sep. 21, 2007.

(56) References Cited

U.S. PATENT DOCUMENTS

| | | | |
|---|---|---|---|
| 5,260,151 A | 11/1993 | Berger et al. | |
| 5,296,255 A | 3/1994 | Gland et al. | |
| 5,367,171 A * | 11/1994 | Aoyama | H01J 37/20 250/442.11 |
| 5,406,087 A * | 4/1995 | Fujiyoshi | B01L 3/508 250/440.11 |
| 5,412,180 A * | 5/1995 | Coombs, III | H01J 37/20 118/725 |
| 5,464,977 A * | 11/1995 | Nakagiri | G03F 7/70666 250/234 |
| 5,698,856 A * | 12/1997 | Frasca | H01J 37/20 250/440.11 |
| 5,714,791 A | 2/1998 | Chi et al. | |
| 5,731,587 A | 3/1998 | DeBattista et al. | |
| 6,297,511 B1 | 10/2001 | Syllaios et al. | |
| 6,300,124 B1 * | 10/2001 | Blumenfeld | B01L 7/52 435/283.1 |
| 6,495,838 B1 * | 12/2002 | Yaguchi | H01J 37/20 250/443.1 |
| 6,538,254 B1 * | 3/2003 | Tomimatsu | H01J 37/3056 250/442.11 |
| 6,657,431 B2 * | 12/2003 | Xiao | G01R 33/0385 324/210 |
| 6,768,124 B2 | 7/2004 | Suzuki et al. | |
| 6,786,716 B1 | 9/2004 | Gardner et al. | |
| 6,809,533 B1 * | 10/2004 | Anlage | G01R 27/2664 324/750.02 |
| 6,812,473 B1 | 11/2004 | Amemiya | |
| 6,828,566 B2 * | 12/2004 | Tomimatsu | G01N 1/28 250/442.11 |
| 7,071,475 B2 * | 7/2006 | Tomimatsu | G01N 1/28 250/442.11 |
| 7,132,673 B2 * | 11/2006 | Fischione | H01J 37/08 204/192.34 |
| 7,138,628 B2 * | 11/2006 | Tomimatsu | G01N 1/28 250/306 |
| 7,145,330 B2 * | 12/2006 | Xiao | B82Y 35/00 250/306 |
| 7,176,458 B2 * | 2/2007 | Tomimatsu | G01N 1/28 250/306 |
| 7,381,968 B2 * | 6/2008 | Tanaka | H01J 37/20 250/310 |
| 7,397,050 B2 * | 7/2008 | Tomimatsu | G01N 1/28 250/311 |
| 7,397,052 B2 * | 7/2008 | Tomimatsu | G01N 1/28 250/492.21 |
| 7,482,587 B1 | 1/2009 | Finch | |
| 7,504,623 B2 * | 3/2009 | Fischione | H01J 37/08 204/192.34 |
| 7,525,108 B2 * | 4/2009 | Tomimatsu | G01N 1/28 250/492.21 |
| 7,798,011 B2 * | 9/2010 | Warren | B82Y 35/00 73/780 |
| 8,334,519 B2 * | 12/2012 | Ono | G01R 31/307 250/306 |
| 8,859,991 B2 | 10/2014 | Nackashi et al. | |
| 8,872,129 B2 | 10/2014 | Damiano, Jr. et al. | |
| 2002/0033695 A1 * | 3/2002 | Xiao | B82Y 35/00 324/244 |
| 2003/0183776 A1 * | 10/2003 | Tomimatsu | G01N 1/28 250/442.11 |
| 2004/0003666 A1 * | 1/2004 | Fischione | H01J 37/20 73/856 |
| 2004/0207396 A1 * | 10/2004 | Xiao | B82Y 35/00 324/244 |
| 2005/0054029 A1 * | 3/2005 | Tomimatsu | G01N 1/28 435/40.5 |
| 2005/0230636 A1 * | 10/2005 | Tanaka | H01J 37/20 250/440.11 |
| 2006/0022148 A1 * | 2/2006 | Fischione | H01J 37/08 250/492.21 |
| 2006/0025002 A1 * | 2/2006 | Zhang | H01J 37/20 439/329 |
| 2006/0097187 A1 | 5/2006 | Zandbergen | |
| 2006/0102850 A1 | 5/2006 | Tokunaga et al. | |
| 2006/0192099 A1 * | 8/2006 | Tomimatsu | G01N 1/28 250/281 |
| 2006/0231776 A1 * | 10/2006 | Tomimatsu | G01N 1/28 250/492.21 |
| 2007/0023701 A1 * | 2/2007 | Fishione | H01J 37/08 250/492.21 |
| 2007/0116600 A1 * | 5/2007 | Kochar | G01N 21/76 422/65 |
| 2007/0145299 A1 * | 6/2007 | Tomimatsu | G01N 1/28 250/492.21 |
| 2007/0145300 A1 * | 6/2007 | Tomimatsu | G01N 1/28 250/492.21 |
| 2007/0145302 A1 * | 6/2007 | Tomimatsu | G01N 1/28 250/492.21 |
| 2007/0180924 A1 * | 8/2007 | Warren | B82Y 35/00 73/780 |
| 2008/0067374 A1 * | 3/2008 | Ono | G01R 31/307 250/310 |
| 2008/0179518 A1 | 7/2008 | Creemer et al. | |
| 2008/0308727 A1 * | 12/2008 | Boguslavsky | G01N 1/286 250/307 |

FOREIGN PATENT DOCUMENTS

| | | | |
|---|---|---|---|
| DE | 202006013471 U1 | 11/2006 | |
| EP | 1939923 A2 | 7/2008 | |
| JP | S50024072 A | 3/1975 | |
| JP | 57095762 U | 6/1982 | |
| JP | S60164761 U | 11/1985 | |
| JP | 7128206 A | 5/1995 | |
| JP | 200177013 A | 3/2001 | |
| JP | 2004045359 A | 2/2004 | |
| JP | 2005114534 A | 4/2005 | |
| JP | 2006203040 A | 8/2006 | |
| JP | 2007303946 A | 11/2007 | |
| NL | WO 2006031104 A1 * | 3/2006 | H01J 37/20 |
| NL | WO 2006031104 A9 * | 10/2006 | H01J 37/20 |
| WO | 2006031104 A1 | 3/2006 | |
| WO | WO 2006031104 A1 * | 3/2006 | H01J 37/20 |
| WO | 2008141147 A1 | 11/2008 | |

OTHER PUBLICATIONS

Zhang, M et al., "In situ transmission electron microscopy studies enabled by microelectromechanical system technology," Journal of Materials Research, 2005, pp. 1802-1807, vol. 20.

Supplementary European Search Report, Mar. 8, 2012.

Zhang, Xiao, et al.; "A Simple Specimen Holder for EBIC Imaging on the Hitachi S800," Microscopy Research and Technique, 1993, pp. 182-183, vol. 26.

International Preliminary Report on Patentability, Nov. 10, 2009.

Butler, E.P., et al.; "Dynamic Experiments in the Electron Microscope," Practical Methods in Electron Microscopy, 1981, pp. 109-355, vol. 9.

Sharma, Renu, et al., Development of a TEM to Study In Situ Structural and Chemical Changes at an Atomic Level During Gas-Solid Interactions at Elevated Temperatures, Microscopy Research and Technique, 1998, pp. 270-280, vol. 42.

European Office Action, Aug. 29, 2013.

Japanese Office Action, Jan. 17, 2013.

(56) References Cited

OTHER PUBLICATIONS

Olson, et al.; "The Design and Operation of a MEMS Differential Scanning Nanocalorimeter for High-Speed Heat Capacity Measurements of Ultrathin Films," Journal of Microelectromechanical Systems, 2003, pp. 355-364, Vo. 12.

Supplementary European Search Report, Jan. 31, 2012.

European Office Action, Nov. 25, 2014.

* cited by examiner

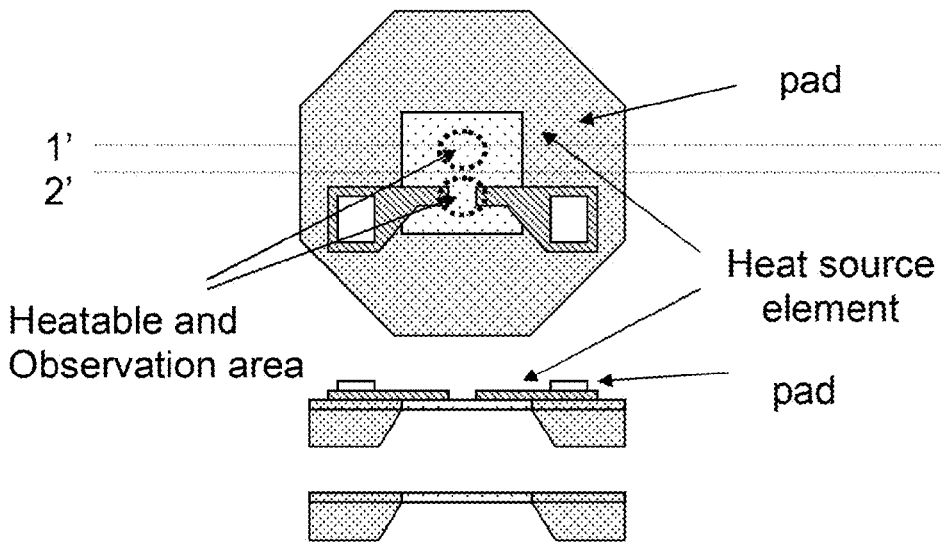
FIGURE 10a
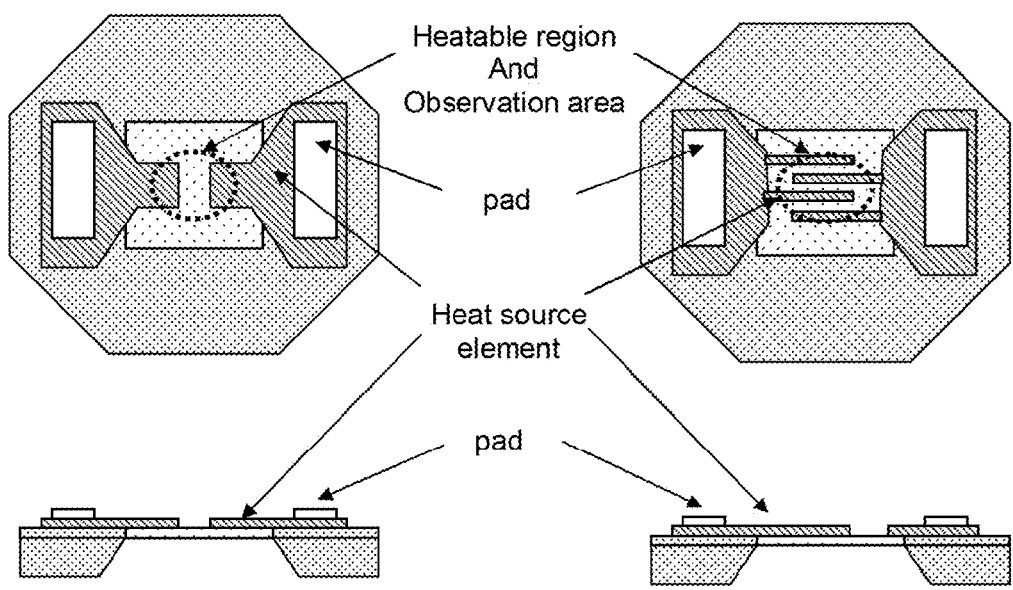
FIGURE 10b          FIGURE 10c

SPECIMEN HOLDER USED FOR MOUNTING SAMPLES IN ELECTRON MICROSCOPES

CROSS REFERENCE TO RELATED APPLICATIONS

This application is a Continuation-in-Part (CIP) and claims priority to U.S. patent application Ser. No. 13/799,871 filed on Mar. 13, 2013 entitled "Specimen Holder Used for Mounting Samples in Electron Microscopes" in the name of David P. Nackashi, et al., which is a divisional of U.S. patent application Ser. No. 12/933,213 filed on Feb. 9, 2011, now U.S. Pat. No. 8,513,621 issued on Aug. 20, 2013, which is a 35 U.S.C. §371 filing claiming priority to International Patent Application No. PCT/US2009/037396 filed on 17 Mar. 2009, which claims priority of U.S. Provisional Patent Application Nos. 61/037,115 filed on 17 Mar. 2008 and 61/085,650 filed on 1 Aug. 2008, all of which are hereby incorporated by reference herein in their entirety. This application is also a CIP and claims priority to U.S. patent application Ser. No. 12/599,339 having a filing date of Dec. 8, 2010 entitled "Microscopy Support Structures" in the name of John Damiano Jr., et al., which is a 35 U.S.C. §371 filing claiming priority to International Patent Application No. PCT/US2008/063200 filed on 9 May 2008, which claims priority of U.S. Provisional Patent Application Nos. 60/916,916 filed on 9 May 2007 and 60/974,384 filed on 21 Sep. 2007, all of which are hereby incorporated by reference herein in their entirety.

FIELD

The invention relates generally to specimen holders used for mounting samples in an electron microscope, e.g., a transmission electron microscope (TEM), a scanning transmission electron microscopy (STEM) and variations of the scanning electron microscopes (SEM) that use traditional TEM-type holders and stages.

BACKGROUND

The specimen holder is a component of an electron microscope providing the physical support for specimens under observation. Specimen holders traditionally used for TEMs and STEMs, as well as some modern SEMs, consist of a rod that is comprised of three key regions: the end, the barrel and the specimen tip (see, e.g., FIG. 1). In addition to supporting the specimen, the specimen holder provides an interface between the inside of the instrument (i.e., a vacuum environment) and the outside world.

To use the specimen holder, one or more samples are first placed on a support device. The support device is then mechanically fixed in place at the specimen tip, and the specimen holder is inserted into the electron microscope through a load-lock. During insertion, the specimen holder is pushed into the electron microscope until it stops, which results in the specimen tip of the specimen holder being located in the column of the microscope. At this point, the barrel of the specimen holder bridges the space between the inside of the microscope and the outside of the load lock, and the end of the specimen holder is outside the microscope. To maintain an ultra-high vacuum environment inside the electron microscope, flexible o-rings are typically found along the barrel of the specimen holder, and these o-rings seal against the microscope when the specimen holder is inserted. The exact shape and size of the specimen holder varies with the type and manufacturer of the electron microscope, but each holder contains these three key regions.

Interfacing semiconductor-based devices with specimen holders for use in electron microscopes has seen limited commercial development. There are, however, a few applications that have either required an electrical interface between the sample and the specimen holder, or have incorporated semiconductor devices in a research environment.

Several electron microscopy techniques, including Electron Beam Induced Current (EBIC), require an electrical contact between a sample and the specimen holder itself. Typically, this is done using a simple screw and metallic clip, which is gently pressed down onto the sample by tightening the screw (see, X. Zhang and D. Joy, "A simple specimen holder for EBIC imaging on the Hitachi S800," *J. Microscopy Res. and Techn.*, Vol. 26(2), pp. 182-183, 1993). A wire is either soldered to the clip or looped around the screw head to provide an electrical path from the sample, through the clip, and to the specimen holder which routes the wire outside of the instrument. This approach is tedious, requiring the user to manually align the clips over the appropriate regions on the device, then manually tighten every screw that is needed to complete an electrical path to the specimen holder. Because of the small size of these screws and the sample itself, this approach takes time and requires a substantial amount of dexterity.

An alternative approach (U.S. Pat. No. 5,124,645) requires a wirebond, or solder joint, to establish a more durable connection between the sample and the specimen tip of a specimen holder. These connections, however, are permanent and do not allow samples to be easily interchanged between experiments. Following an experiment, to exchange samples, the specimen holder must be placed back into a wirebond machine or soldering must again be performed to create a new electrical connection with the new sample. This approach is tedious, requires great dexterity, and is likely to damage the specimen tip after repeated use.

An approach developed at the University of Illinois (U.S. patent application Ser. No. 11/192,300) addresses some of these concerns. This approach allows a semiconductor device to be mounted in a specimen tip, making as many as twelve simultaneous electrical connections between the holder and the device. A frame (generally U-shaped) aligns the device and baseplate with electrical spring contact fingers and provides a rigid surface against which the device is pressed, providing stability and forming electrical contacts between the device and the specimen holder. The baseplate is the component of the specimen tip that provides a stable surface upon which the device can be mounted, and contains electrical spring contact fingers in complementary positions to the device, which when aligned using the frame, make contacts simultaneously between the baseplate and the device. Disadvantageously, spring contact fingers such as these are delicate and more difficult to manufacture. Removing the device from the baseplate completely exposes the spring clips and presents an opportunity to accidentally bend or break these fingers, compromising the electrical connections.

Considering the disadvantages of the prior art, a novel specimen holder is needed, wherein said specimen holder eliminates the need for delicate spring contact fingers and provides a simple method for repeatedly mounting and exchanging devices without disassembly or soldering.

SUMMARY

The present invention relates generally to a novel specimen holder which provides mechanical support for specimen support devices and as well as electrical contacts to the specimens or specimen support devices.

In one aspect, an electron microscope specimen holder is described, said specimen holder comprising a body, a clipping means, and at least one guide mechanism. The specimen holder may further comprise a spring or a spring cantilever.

In another aspect, an electron microscope specimen holder is described, said specimen holder comprising a body, a clipping means, and at least one guide mechanism, wherein the clipping means comprise an article of manufacture having a top surface, a bottom surface, a first end, a securing means, a second end, and at least one electrical contact integrated on and/or in the bottom surface of the article. The securing means may comprise one of a pivot positioned between the first end and the second end of the article; a fixed point at or near the first end of the article and wherein the article is flexible; or a set screw. The specimen holder may further comprise a spring or a spring cantilever.

In each of these aspects, the specimen holder may further comprise a specimen support device mechanically secured between the clipping means and the body. The specimen support device may comprise a frame, at least one electrical lead and at least one membrane region.

In still another aspect, a method of providing an electrical contact between a specimen and a specimen holder of an electron microscope is described, said method comprising:
positioning a specimen on a specimen support device, wherein the specimen support device comprises a frame, at least one electrical lead and at least one membrane region; and
inserting the specimen support device in a specimen holder, wherein the specimen holder comprises a body, a clipping means, and at least one guide mechanism, wherein the clipping means comprise at least one electrical contact integrated on and/or in a bottom surface of the clipping means; and wherein at least one electrical lead of the device substantially contacts at least one electrical contact of the clipping means.

Yet another aspect relates to a method of using a specimen holder in electron microscopy, said method comprising:
positioning a specimen support device in a specimen holder as described herein; and
inserting said specimen holder in an electron microscope.

Other aspects, features and advantages of the invention will be more fully apparent from the ensuing disclosure and appended claims.

BRIEF DESCRIPTION OF FIGURES

In FIG. 9A, direct heating is applied, and the heatable region and observation region are identical. In FIG. 9B, indirect heating is applied, and the observation region is adjacent to the heatable region.

FIG. 10a illustrates a device of the invention with two heatable and observation regions on the same membrane, in plan view and cross-sectional view.

FIG. 10b illustrates heat source elements designed as a simple polygon, in plan view and cross-sectional view FIG. 10c illustrates heat source elements as a complex structure with multiple fingers interdigitated with one or more other heat source elements, in plan view and cross-sectional view.

DETAILED DESCRIPTION

Figure 1:
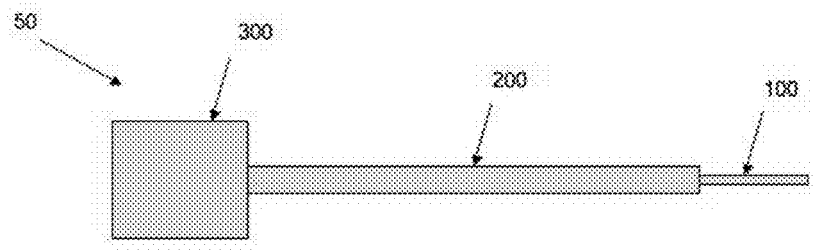
FIG. 1 shows a schematic of a generic specimen holder (50). The specimen holder is comprised of three regions: the tip (100), the barrel (200), and the end (300).

The present invention generally relates to novel specimen holders, methods for interfacing samples at the tip of the specimen holder, and uses of the novel specimen holder. It is to be understood that the specimen holder and specimen holder interface described herein are compatible with and may be interfaced with the semiconductor specimen support devices such as those disclosed in U.S. Patent Application Nos. 60/916,916 and 60/974,384, which are incorporated herein by reference in their entireties and which are described below. It should be appreciated by one skilled in the art that alternative specimen support devices may be interfaced with the specimen holder described herein. The specimen holder provides mechanical support for one or more specimens or specimen support devices and may also provide electrical contacts to the specimens or specimen support devices. The specimen holder can be manufactured with tips, barrels and ends of various shapes and sizes such that the specimen holder fits any manufacturer's electron microscope.

Semiconductor Specimen Support Devices

As defined herein, "semiconductor" means a material, such as silicon, that is intermediate in electrical conductivity between conductors and insulators.

As defined herein, "device" means a structure used to either contain gases and/or control temperatures around a specimen (two types of devices: a window device and a temperature control device).

As defined herein, "specimen" means the object being studied in the electron microscope generally arranged on either side of the device (e.g., nanoparticle, catalyst, thin section, etc.).

As defined herein, "window device" means a device used to create a physical, electron transparent barrier on one boundary of the E-cell and the vacuum environment of the electron microscope (generally a silicon nitride-based semiconductor micro-machined part).

As defined herein, "temperature control device" means a device used to control the temperature around the specimen.

As defined herein, "frame" means a rigid region around the perimeter of a device that is used to provide mechanical support to the entire device structure (preferred embodiments include a silicon frame selectively etched using KOH, a silicon frame selectively etched using RIE, a silicon frame selectively etched using DRIE, or a silicon frame released from an SOI wafer).

As defined herein, a "membrane region" corresponds to unsupported material comprised, consisting of, or consisting essentially of carbon, silicon nitride, SiC or other thin films generally 1 micron or less having a low tensile stress (<500 MPa), and providing a region at least partially electron transparent region for supporting the at least one specimen. The membrane region may include holes or be hole-free. The membrane region may be comprised of a single material or a layer of more than one material and may be either uniformly flat or contain regions with varying thicknesses.

As defined herein, "element" means a component used on a device, typically on or near the membrane, that enhances or adds capability to the device (e.g., heat source element, mechanical element, heat sink element).

As defined herein, "mechanical element" means a component generally used to strengthen and provide rigidity to the membrane (e.g., reinforced membrane embodiment).

As defined herein, "heat source element" means a component made up of two or more electrodes through which a current is forced, creating heat through Joule heating (e.g., in a temperature control device a heat source element may be used to effect direct heating—the membrane is the heat source element directly heating the specimen (bilayer stack); in a temperature control device a heat source element may be used to effect indirect heating—flux carries the heat across the membrane to the specimen. Many different spatial designs exist).

As defined herein, "heat sink element" means a component made up of one or more electrodes used to passively remove heat from the membrane region by providing path(s) for higher flux to occur away from the membrane (many different spatial designs).

As defined herein, "temperature sense element" means a component used to directly measure the temperature on the device (either frame or membrane, but typically membrane; window device and/or temperature control device).

As defined herein, "electrical sense element" means a component used to directly measure current or voltage on the device (either frame or membrane, but typically membrane on the temperature control device).

As defined herein, "mechanical sense element" means a component used to measure deflection or rupture of a membrane (window device and/or temperature control device).

As defined herein, "pad" means an area on an electrode used to provide an interface between the holder and the device.

As defined herein, "refractory metals" correspond to tungsten, niobium, tantalum, molybdenum, rhenium, osmium, iridium, rhodium, ruthenium, technetium, hafnium, zirconium, vanadium, chromium, platinum, palladium and alloys thereof.

Semiconductor specimen support devices such as those disclosed in U.S. Patent Application Nos. 60/916,916 and 60/974,384 include devices generally constructed using semiconductor materials and contain at least a frame and one membrane region. The device may also contain a frame and multiple membrane regions. A device may or may not include one or more additional elements, such as heat source elements and mechanical elements.

A membrane region is a portion of the semiconductor specimen support device structure generally in the center of each device that is unsupported by the frame. The membrane region may consist of one or more thin films, including semiconductor materials as well as other deposited films such as carbon or graphene. The membrane region(s) in each device are created from membrane materials, are generally less than 1 micron in thickness, are robust, insulating or conductive, and can be constructed using a variety of semiconductor techniques in combination with other deposition and float-down techniques. In general, membrane materials are deposited onto the frame material and have a tensile stress profile to keep the subsequently formed membrane region(s) pulled tightly across the frame. One embodiment of a membrane region is a thin, amorphous silicon nitride film as the membrane material so that the membrane region is nearly electron transparent, and another embodiment of a membrane region is a thin, silicon carbide film as the membrane material. In this embodiment the membrane region is not required to be electron transparent although it can be electron transparent or partially electron transparent. In this embodiment the membrane material provides a surface upon which a specimen can be placed and the temperature controlled. Other membrane materials that can be used to create membrane regions include boron nitride, graphene, carbon, aluminum nitride, silicon dioxide and silicon. Membrane regions may or may not contain additional elements directly integrated onto or placed upon their top or bottom surface. When a membrane region is constructed from a conductive material, a thin insulating material such as silicon dioxide or silicon nitride may be placed between the frame and the material on the frame that is contiguous with the membrane region to prevent the creation of a shorting electrical path through the frame. Likewise, when a membrane region is constructed from a conductive material, a thin insulating material such as silicon dioxide or silicon nitride may be deposited or placed on the top surface of the membrane material to prevent the creation of a shorting electrical path.

A membrane region may either be comprised of a continuous film of membrane material or may be comprised of a stack of films of membrane materials, or may contain one or more holes perforating the membrane material from the top to the bottom surface or may contain one or more dimples in its top or bottom surface. Holes perforating the membrane region are generally less than 10 microns across, but can be as large as hundreds of microns. Holes are generally circular in shape, but may also be squares, diamonds, rectangles, triangular or polygonal. Holes are generally used to create regions in a membrane region that are completely electron transparent, upon which a specimen is placed. Dimples in the membrane material within the membrane region are generally less than 100 microns across, but can be as large as hundreds of microns. Dimples are generally circular in shape, but may also be squares, diamonds, rectangles, triangular or polygonal. Dimples are generally used to create regions in a membrane region that are relatively more electron transparent than the non-dimpled membrane regions.

Membranes regions within devices that are used to control a specimen temperature will have a distinct heatable region within the membrane region that is generally in the center of the membrane region, and is the area where the specimen temperature is primarily controlled. This heatable region is defined by the heat generated using the heat source element. More than one heatable region may be present upon each membrane region. A key differentiating feature of this invention over other approaches is the membrane region itself being used as both the specimen support as well as the heatable region (i.e., the source of heat). This approach minimizes the distance between the specimen and the heatable region, allowing the sample to be in very close proximity (less than 500 nm) from the heat source. This greatly reduces the ambiguity in other systems that generate the heat in regions away from the specimen and rely solely on heat flux through materials with poor heat conductivity to heat the specimen indirectly.

A membrane observation region is the location on the membrane region where the electron beam can be used to analyze a specimen, and is generally the location where the specimen is placed. This observation region is typically the same as the size and shape of the entire membrane region itself, but in some instances may be considered as only the heatable region or as a subset of the membrane region.

Figure 9:
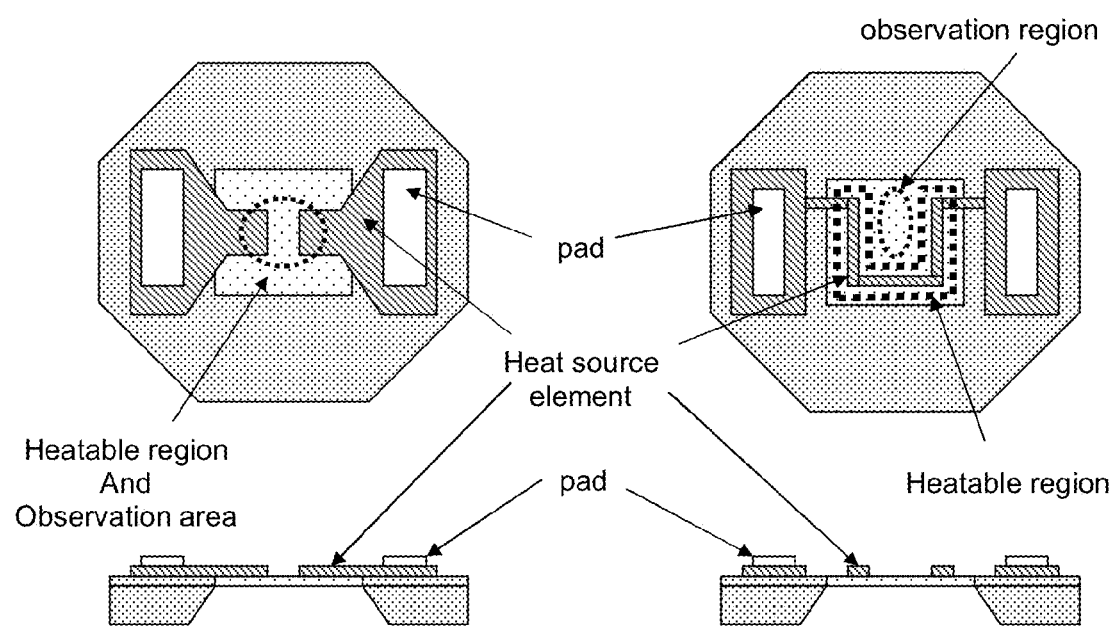
FIG. 9 illustrates the heat source element of a device of the invention in plan view and cross-sectional view.

In devices used to control the temperature of a specimen, heat is generated using an element on the membrane. Heat source elements are comprised of electrodes of sufficiently high conductivity to allow current flow for Joule heating at voltages generally less than 200V. Heat source elements are generally fabricated or placed above the frame material and are generally created from either the membrane material(s), a combination of the membrane material(s) plus subsequent material(s) deposited, grown or placed on top of the membrane material(s), or material(s) deposited, grown or placed on top of the membrane material. The presence of two or more heat source elements defines at least one heatable region on the membrane region. The heat source element(s) can extend onto the membrane region. In the case of direct heating, the heatable region and the observation region are the same. In the case of indirect heating, the observation region(s) are separate regions from the heatable region(s). Heat source elements may occupy a large area on the frame and an electrical pad may be used to facilitate electrical contact between the heat source element and the electron microscope holder. The heat source element may be more narrow near the membrane region so as to confine the electrical current path and to facilitate Joule heating across the membrane region. A preferred embodiment for direct heating is to place two heat source elements in a flanking position across the membrane region, with an observation region defined between them. The observation region is also the heating region, which is an area on the membrane region located between (and not including) the heat source elements. Examples of heat source elements are illustrated in FIGS. 9 and 10. The use of a membrane material that is at least partially conductive allows Joule heating to occur within the membrane, specifically, in the observation region that is supporting the specimen. This makes the membrane observation region itself the heatable region, and is a key differentiating feature of this invention over other approaches. Directly heating the membrane (which supports the specimen) by forcing current through the material using heat source elements minimizes the distance between the heatable region and the specimen, generally to distances less than about 500 nm. This removes the ambiguity between knowing the temperature of the heater and temperature of the sample.

Heat source elements are generally deposited and patterned on the surface of the device, and are located both on the frame and the membrane. They are manufactured using a material that is highly conductive. Preferred materials for manufacturing heat source elements are silicon carbide and refractory metals.

One preferred embodiment is to manufacture the membrane region using a stack of material with different electrical conductivities such as multiple layers of silicon carbide with different doping profiles in each adjacent layer, and define two or more heat source elements by patterning the membrane material stack. The membrane material(s) may vary in conductivity with thickness, generally from less conductive in the material closest to the frame to more conductive in the material furthest from the frame. Another embodiment is to manufacture the membrane region using a conductive material such as silicon carbide, and then deposit and pattern two or more heat source elements in a more conductive material such as a refractory metal deposited, placed, or grown above the membrane material. In both of these embodiments, when current is forced from one or more heat source elements to one or more other heat source elements through the membrane material, Joule heating will occur in the membrane material. The heat source elements may be designed in a variety of ways to selectively expose areas in the membrane region that are less conductive than the heat source elements. For example, the size and shape of each heat source element, the spatial relationship between the heat source element(s) and the membrane region(s), and the distance between heat source elements can all be designed to control the uniformity of heat on the membrane region and the localization of heat between adjacent membrane regions. Heat source elements may be designed as a simple polygon, as shown in FIG. 10B, or as a complex structure with multiple fingers interdigitated with one or more other heat source elements, as shown in FIG. 10C.

The heat source heatable region is the region on the membrane where the majority of the heating occurs. The heat source observation area is an area on the membrane region where the specimen is placed to facilitate observation using an electron microscope, and it is a region whose temperature is controlled using a heat source element(s). In direct heating, the heat source observation area is the area of the membrane region between two or more heat source elements, and this area is both the heat source observation area and the heatable region, heated by Joule heating from current flowing between the heat source elements. In indirect heating, the heat source element is the heat source heatable region and the heat source observation region is located nearby being heated by heat generated in the heatable region and transferred by thermal conduction to the heat source observation region. Importantly, in indirect heating, the membrane is a thermal conductor, not an insulator. Moreover, the heaters of the invention use a semiconductor material as the heater and not spiral metal heaters as found in prior art devices.

Electrical contacts from the holder to the device are required for any element where an electrical signal is used to measure or stimulate some response of or on the device. Electrical contacts are generally used in conjunction with electrical source or sense elements. Electrical contacts are made by defining pad regions, and the pad regions are generally directly on the surface of the respective element itself and in a region over the frame. These pad regions are areas generally greater than about 100 microns by about 100 microns defined on the element either by 1) a patterned region of material where the pad material is different from the element material, or 2) a patterned region of the element where the pad region is comprised of the same material as the element material. The use of another material is preferred when a good and/or ohmic electrical contact cannot be achieved through a physical contact between the holder and the element material. If the element material is a metal such as tungsten, the pad region could simply be a large area within that element on the frame region. If the element material is a semiconductor or ceramic such as silicon carbide, a metal such as gold, nickel or tungsten could be used. There may be multiple pads per element, and multiple elements per device.

Figure 11:
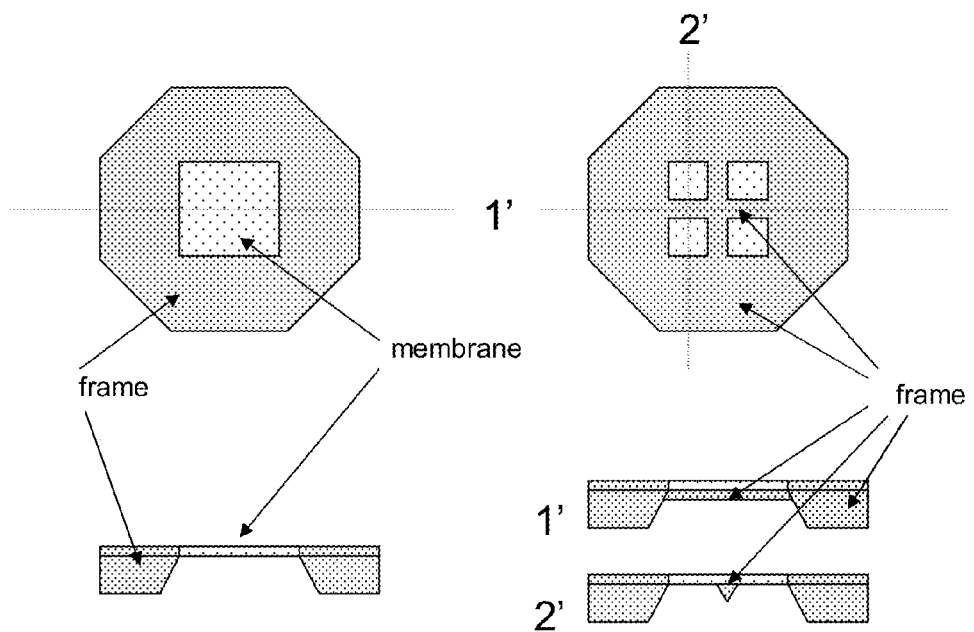
FIG. 11 illustrates two embodiments of frame design of the devices of the invention in plan view and cross-sectional view.

Each device has a frame, which is a thick region generally around the perimeter of the device. The frame gives mechanical support to the device to allow for handling, and provides a strong surface to support the membrane region and allow for good contact between the device and the holder. It will also provide a level of thermal isolation between membrane regions on a device with multiple membrane regions. Frames are typically about 12 microns thick or greater, with preferred embodiments at about 12, 25, 50, 200 and 300 microns thick. The frame region is generally outside the observation region of the device. When multiple membranes are present on a device, the frame located between membranes may be thinner than the frame at the perimeter of the device. The frame region of a device is illustrated in FIG. 11. The preferred frame material is single crystal silicon, although frames may also be made from polysilicon, quartz or fused silica. Frames may be circular, rectangular, square or polygonal at the perimeter. For rectangular or square frames, facets will generally be present at the corners. In devices with multiple membrane regions, the frame will also exist between the membrane regions to provide mechanical support as well as thermal isolation when used as a temperature control device. The membrane regions may also be square, rectangular, circular or polygonal. One preferred embodiment is to have a rectangular or square frame with one or more rectangular or square membrane regions near the center of the device. The frame at the perimeter would be slightly thicker than the frame that exists between the membrane regions. Another embodiment is a round frame at the perimeter, with either one or more round or square membrane regions. Two embodiments are shown in FIG. 11.

Accordingly, one embodiment of a semiconductor specimen support device is a temperature control device, which is a device that contains at least one heat source element, and is used to control the temperature in a defined observation region on the membrane region. Multiple heat source elements may be present, allowing for multiple heatable regions and multiple observation regions. A temperature control device may also contain multiple heat source elements and multiple membrane regions. The frame regions between the multiple membranes will provide mechanical support to the membrane regions and thermal isolation between heatable and observation regions within the different membrane regions. The temperature control device may also contain additional elements to add capabilities, such as electrical sense, mechanical support and at least one heat sink.

Another embodiment of a semiconductor specimen support device is a window device which contains a frame, a membrane region and may or may not contain mechanical elements. They are used to either support a specimen for imaging, or to confine an environment around a specimen in an environmental cell as described below.

The semiconductor specimen support devices provide the capability to achieve atomic resolution of a specimen in an electron microscope including a transmission electron microscope (TEM). Micron-scale openings formed in the membrane region provide electron beam-transparent regions for analysis and avoid any potential scattering from the membrane material comprising the membrane. Specimen preparation can be enhanced by the robustness of the device and membrane material, which allows for thorough cleaning before imaging to reduce or remove the background carbon peak in EELS. The robust nature of the device allows specimens to be directly deposited on the film in a furnace or even a chemical solution. This ability to withstand direct deposition of the specimen decreases specimen preparation time and increases resolution.

The devices of the invention are mechanically and electrically mounted to a holder itself.

Specimen Holders

As defined herein, a "spring" corresponds to any object that has a spring constant (k) and which exerts a force onto the specimen support device when it is loaded in the specimen holder. The spring may or may not observe Hooke's law ($F=-kx$) depending on the material of construction.

As defined herein, a "hinge" connects two solid objects, in the present case the insulating clip and the mounting surface, typically allowing only a limited angle of rotation between them. Two objects connected by a hinge rotate relative to each other about a fixed axis of rotation. It is also contemplated herein that the "hinge" may be one or two fulcrums attached to the mounting surface, wherein the clip is flexible.

The present application improves on the prior art in several ways: (1) by eliminating the required use of a delicate spring contact finger, (2) by providing a method for accommodating semiconductor devices that are of various shapes and sizes without the need to machine frames and custom parts to align different devices geometries, and (3) by providing a simple method for mounting and exchanging devices and making electrical contacts to devices without the need for partially disassembling the specimen tip (e.g., removing screws or other small parts).

More specifically, rather than using spring contact fingers (bent slightly at their tips) to separately promote contact with each pad on the device, the specimen holder described herein includes at least one electrode placed on the bottom of an insulating clip, wherein the insulating clip with integrated electrode(s) provides simultaneous mechanical force to all electrodes, simultaneously presses the electrode(s) against contact pads on the device and provides mechanical force for securing the device in place for imaging. Clips and springs used in this application separately provide the mechanical force required to stabilize the device to the specimen holder, and are not used for electrical contacts between the device and the holder. Preferably, the springs are distally positioned along the insulating clip relative to the electrical contacts. This allows the electrical contacts on the clips to be manufactured using planar processes such as, but not limited to, precision machining, lithographic and/or electroplating processes.

Using the specimen holder described herein, only one side of the device is required to have contact pads matching the electrode pitch and width in order to line up with the electrodes underneath the clip. This design improves upon prior art in that it allows a variety of device lengths and shapes to be mounted into the specimen tip. This specimen holder also allows a device to be mounted quickly and easily, making both physical and electrical contacts, without the need to partially disassemble the specimen tip to mount the device.

Figure 2A:
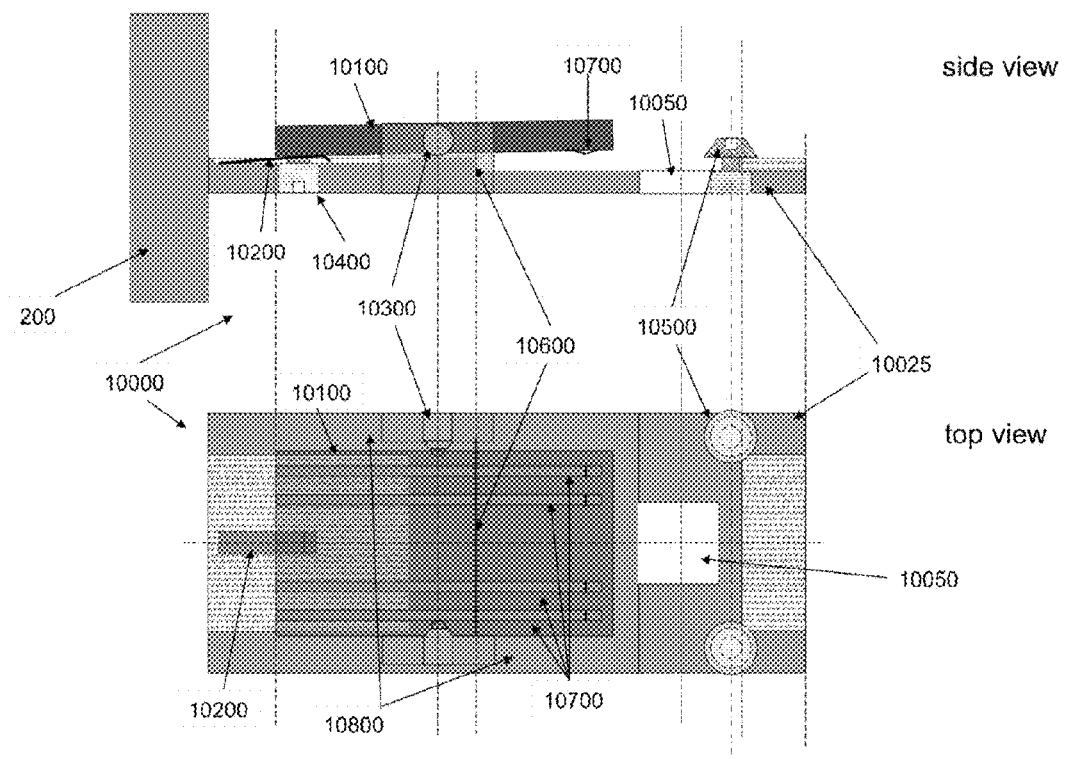
FIG. 2A shows one embodiment of the tip region of a specimen holder described herein wherein the holder tip (10000) shows a clamping mechanism in an open state ready to receive a specimen support device.
Figure 2B:
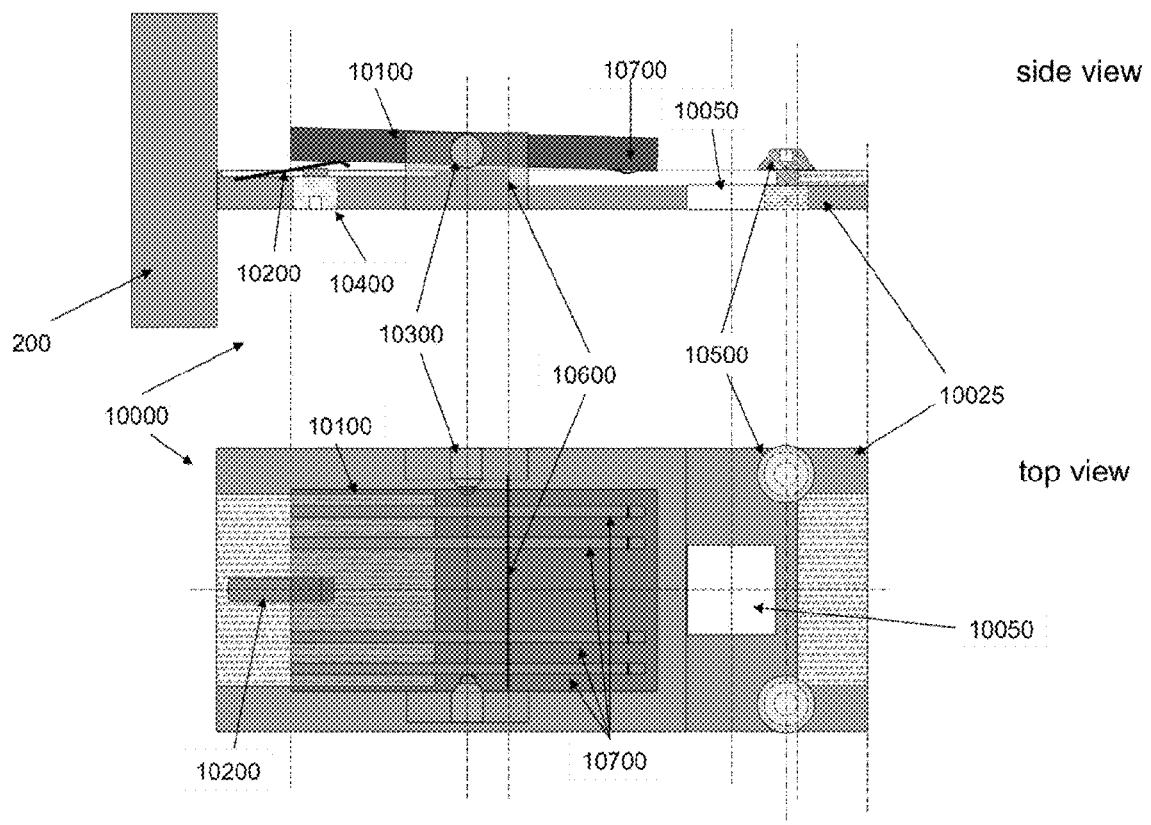
FIG. 2B shows one embodiment of the tip region of a specimen holder described herein wherein the holder tip (10000) shows a clamping mechanism in a closed state without a specimen support device.
Figure 2C:
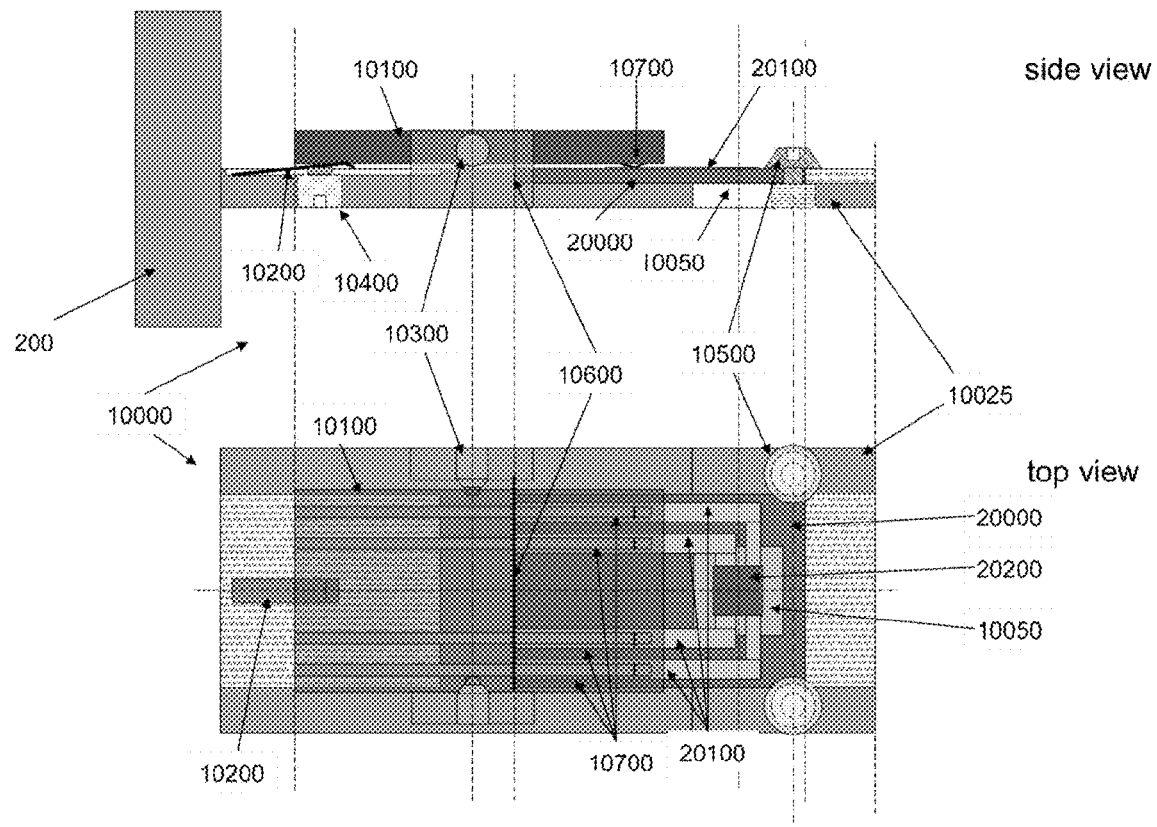
FIG. 2C shows one embodiment of the tip region of a specimen holder described herein wherein the holder tip (10000) shows a clamping mechanism in a closed state with a specimen support device.

One embodiment of the tip region of a specimen holder is shown is FIGS. 2A, 2B and 2C. FIG. 2A shows the tip region of a specimen holder wherein the holder tip (10000) includes a clamping mechanism in an open state ready to receive a specimen support device. FIG. 2B shows the tip region of the specimen holder of FIG. 2A wherein the holder tip (10000) is in a closed state without a specimen support device. FIG. 2C shows the tip region of the specimen holder of FIG. 2A wherein the holder tip (10000) is in an closed state with a specimen support device. In each of these figures, the clamping mechanism is comprised of a clip (10100), spring (10200), hinges (10300), set screw (10400), guide mechanism (10500), depth stop (10600), and at least one electrical contact (10700). The holder tip is comprised of a body (10025), a viewing region (10050), and the clamping mechanism. In FIG. 2C a device is loaded into the tip and held in place by the clamping mechanism. The device is generally comprised of a frame (20000), electrical leads (20100), and a membrane region (20200).

In the clamping mechanism, the clip (10100) acts as a lever, the spring (10200) provides constant tension to the clip, the hinges (10300) allow the clip to pivot about the hinge, the set screw (10400) prevents the spring (10200) from being over-compressed when a device is loaded, and the guide mechanism (10500), such as guide screws, guide pins, or guide posts, provides lateral alignment to a device as it is loaded. When a device is completely loaded, the depth stop (10600) provides a means both to align the electrical contacts of the specimen holder (10700) to electrical leads of a device (20100) and to align the viewing region of the specimen holder tip (10050) with the membrane region of a device (20200). It should be appreciated by one skilled in the art that the electrical contacts of the specimen holder (10700) may extend from one length of the clip to the other or may be present in shorter sections so long as the electrical contacts are present for contact with the electrical leads of the device (20100).

The resting position for the clamping mechanism is shown in FIG. 2B where a spring (10200) pushes upward at one end of the clip (10100), resulting in downward pressure created at the opposite end of the clip where the clip pivots at a set of hinges (10300). The hinge is mounted to a planar mounting surface (10800), said mounting surface extending from the barrel to at least the end of the clip and possibly further. When this mounting surface extends beyond the clip, a viewing region (10050) will typically be included therein just beyond the clip.

To mount the device, downward pressure is placed on the spring end of the clip, which lifts the opposite end above the surface to a level at least as high as the thickness of the device, and typically higher, for example, greater than 1 mm (see FIG. 2A), although less than 1 mm is contemplated. The device is either placed in between the clip and the mounting surface manually, or slid underneath the clip along the mounting surface using the guide screws and depth stop as guidance. Once the device is in position, the pressure on the spring is released and the device is secured manually to the specimen tip (see FIG. 2C).

Electrical contacts from the holder to the device, typically in a range from 2 to 12 electrical contacts (10700), may be provided by the integrated conducting wires or paths underneath the clip. These electrical contacts are electrically isolated from each other and from the clip itself (if the clip is made of a conductive material). When electrical pads exist on the device, the guide mechanism and depth stop will align the device with the clip to allow the electrical contacts from the clip and the pads from the device to contact one another when downward pressure on the clip is released. This will allow both mechanical pressure and electrical connections to be made in a novel, easy to operate design. The electrical contacts will extend from the clip to the barrel, down the barrel to the end, and to a connector that exists at the specimen holder end that can be mated with a plug outside the microscope and connected to a power supply to provide voltage or current through the holder and interface to the specimen support device. Each conductor will remain isolated from each other as well as the three components of the specimen holder.

Figure 3A:
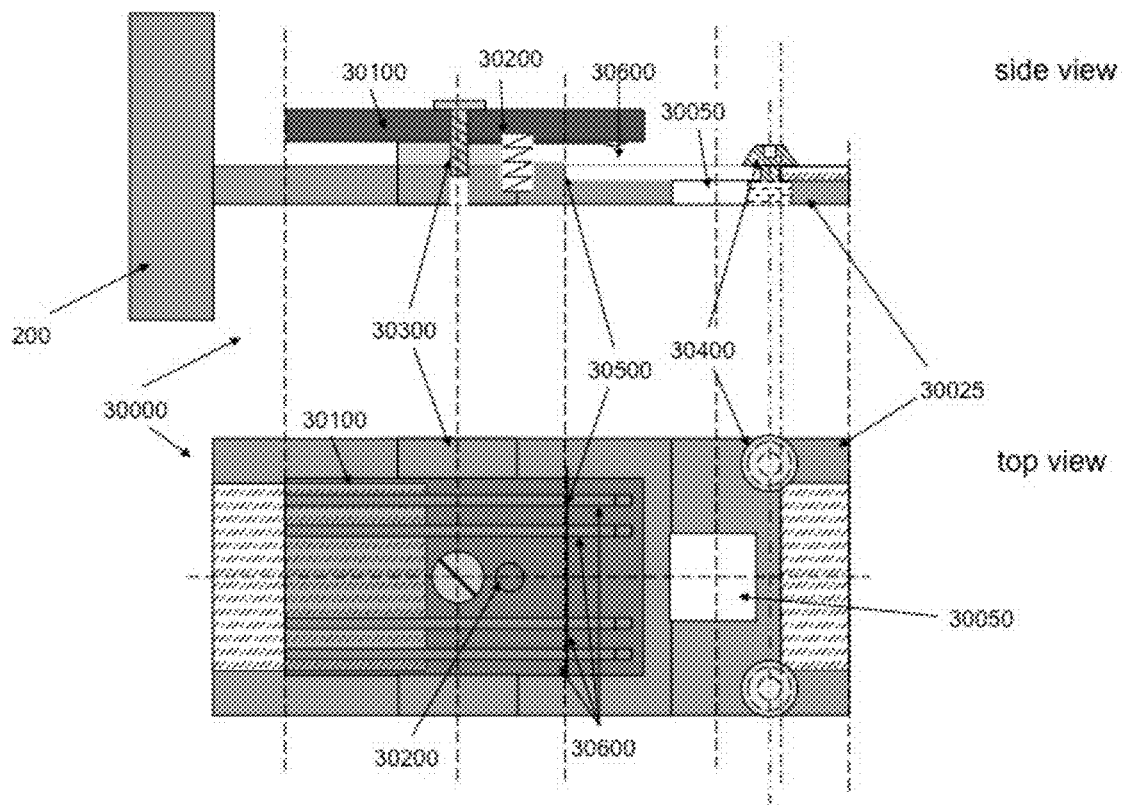
FIG. 3A shows a second embodiment of the tip region of a specimen holder described herein wherein the holder tip (30000) shows a clamping mechanism in an open state ready to receive a specimen support device.
Figure 3B:
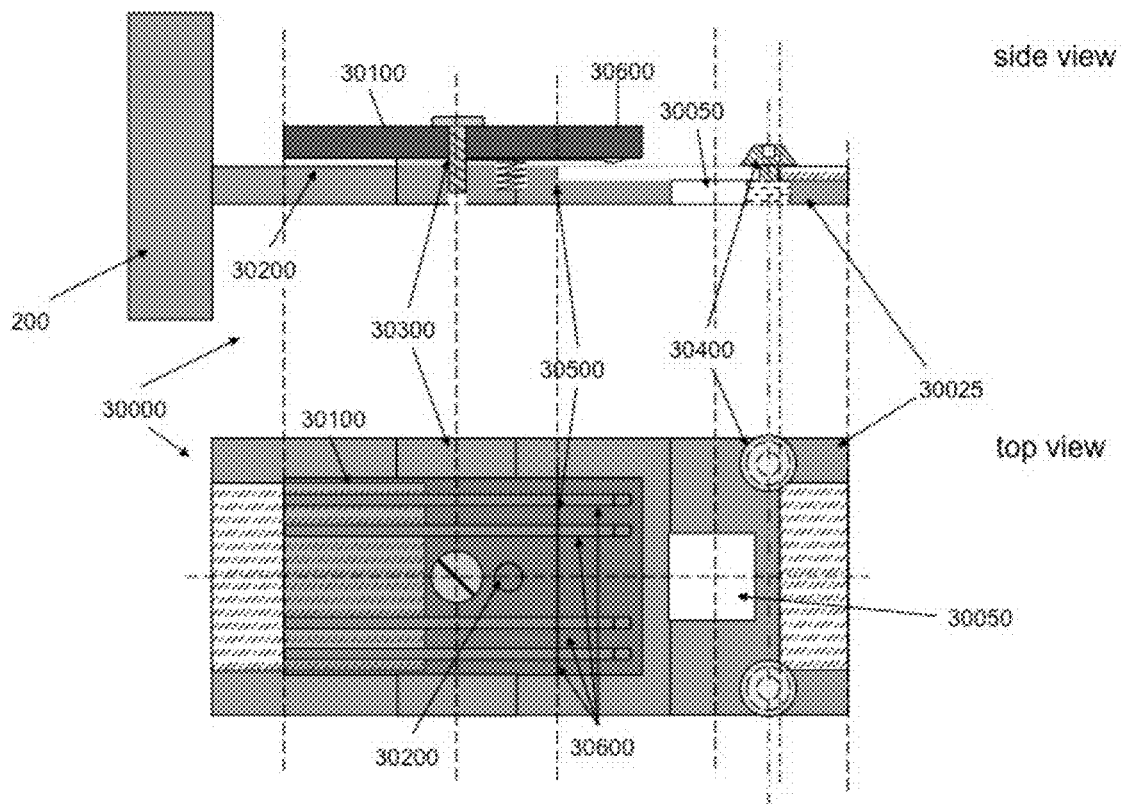
FIG. 3B shows a second embodiment of the tip region of a specimen holder described herein wherein the holder tip (30000) shows a clamping mechanism in a closed state without a specimen support device.
Figure 3C:
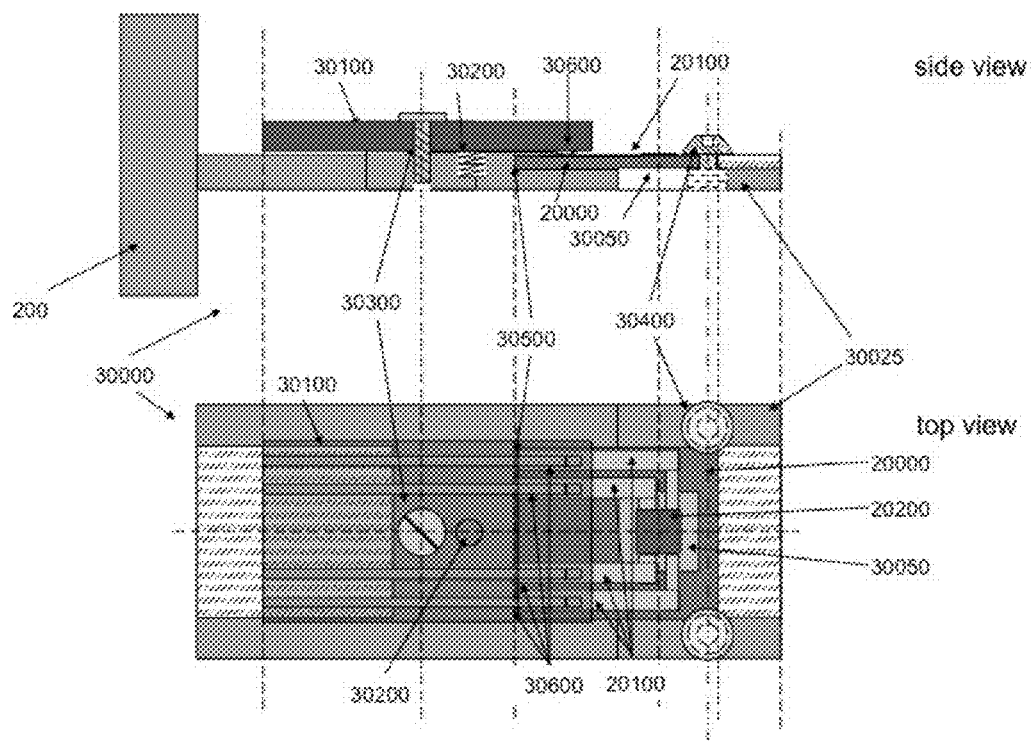
FIG. 3C shows a second embodiment of the tip region of a specimen holder described herein wherein the holder tip (30000) shows a clamping mechanism in an closed state with a specimen support device.

Another embodiment of the tip region of a specimen holder is shown in FIGS. 3A, 3B, and 3C. FIG. 3A shows the tip region of a specimen holder of the present invention where the holder tip (30000) includes a clamping mechanism in an open state ready to receive a specimen support device. FIG. 3B shows the tip region of the specimen holder of FIG. 3A where the holder tip (30000) is in a closed state without a specimen support device. FIG. 3C shows the tip region of the specimen holder of FIG. 3A where the holder tip (30000) is in a closed state with a specimen support device. In each of these figures, the clamping mechanism is comprised of a clip (30100), spring (30200), locking screw (30300), guide mechanism (30400), depth stop (30500), and at least one electrical contact (30600). The holder tip is comprised of a body (30025), a viewing region (30050), and the clamping mechanism. In FIG. 3C a device is loaded into the tip and held in place by the clamping mechanism. The device is generally comprised of a frame (20000), electrical leads (20100), and a membrane region (20200).

In the clamping mechanism, the clip (30100) acts as a clamp, the spring (30200) provides constant tension to the clip, the locking screw (30300) allows the clip to move up and down parallel to the plane of the body (30025), the guide mechanism (30400), such as guide screws, guide pins, or guide posts, provide lateral alignment to a device as it is loaded. When a device is completely loaded, the depth stop (30500) provides a means both to align the electrical contacts of the specimen holder (30600) to electrical leads of a device (20100) and to align the viewing region of the specimen holder tip (30050) with the membrane region of a device (20200). It should be appreciated by one skilled in the art that the electrical contacts of the specimen holder (30600) may extend from one length of the clip to the other or may be present in shorter sections so long as the electrical contacts are present for contact with the electrical leads of the device (20100).

The open position for the clamping mechanism is shown in FIG. 3B where a spring (30200) pushes upward at one end of the clip (30100), resulting in downward pressure pushing at the opposite end of the clip. The clip can be raised or lowered by a locking screw (30300) and when raised, the force exerted by the spring is enough to ensure that the front of the clip is raised enough to allow a specimen support device to be loaded into the holder.

To mount the device, the locking screw is turned to raise the clip to a level at least as high as the thickness of the device, and typically higher, e.g., greater than 1 mm (see FIG. 3A), although less than 1 mm is contemplated. The device is either placed in between the clip and the surface manually, or slid underneath the clip along the surface using the guide screws and depth stop as guidance. Once the device is in position, the locking screw is turned to lower the clip so that the clip secures the device to the specimen tip (see FIG. 3C).

Electrical contacts from the holder to the device, typically in a range from 2 to 12 electrical contacts (30600), may be provided by the integrated conducting wires or paths underneath the clip. These electrical contacts are electrically isolated from each other and from the clip itself (if the clip is made of a conductive material). When electrical pads exist on the device, the guide screws and depth stop will align the device with the clip to allow the electrical contacts from the clip and the pads from the device to contact one another when downward pressure on the clip is released. This will allow both mechanical pressure and electrical connections to be made in a novel, easy to operate design. The electrical contacts will extend from the clip to the barrel, down the barrel to the end, and to a connector that exists at the specimen holder end that can be mated with a plug outside the microscope and connected to a power supply. Each conductor will remain isolated from each other as well as the three components of the specimen holder.

Figure 4A:
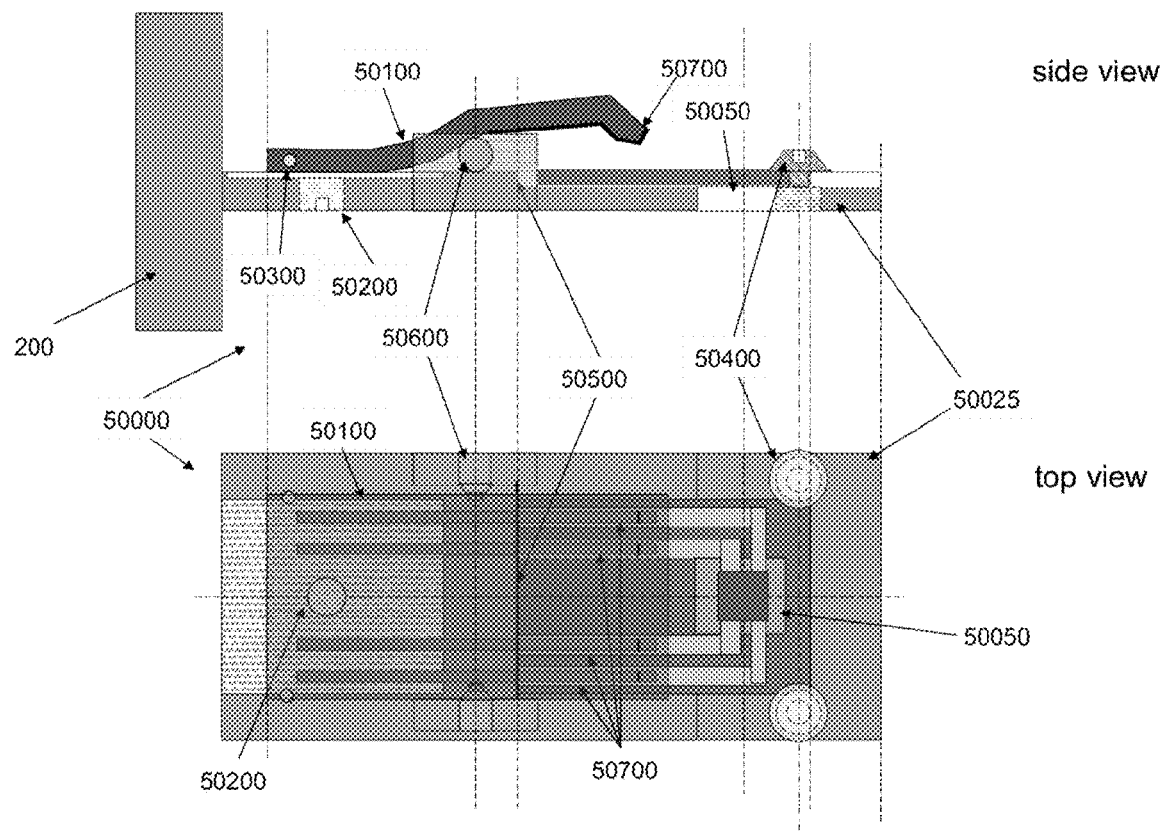
FIG. 4A shows a third embodiment of the tip region of a specimen holder described herein wherein the holder tip (50000) shows a flexing mechanism ready to receive a specimen support device, wherein the fulcrum is a two-piece fulcrum.
Figure 4B:
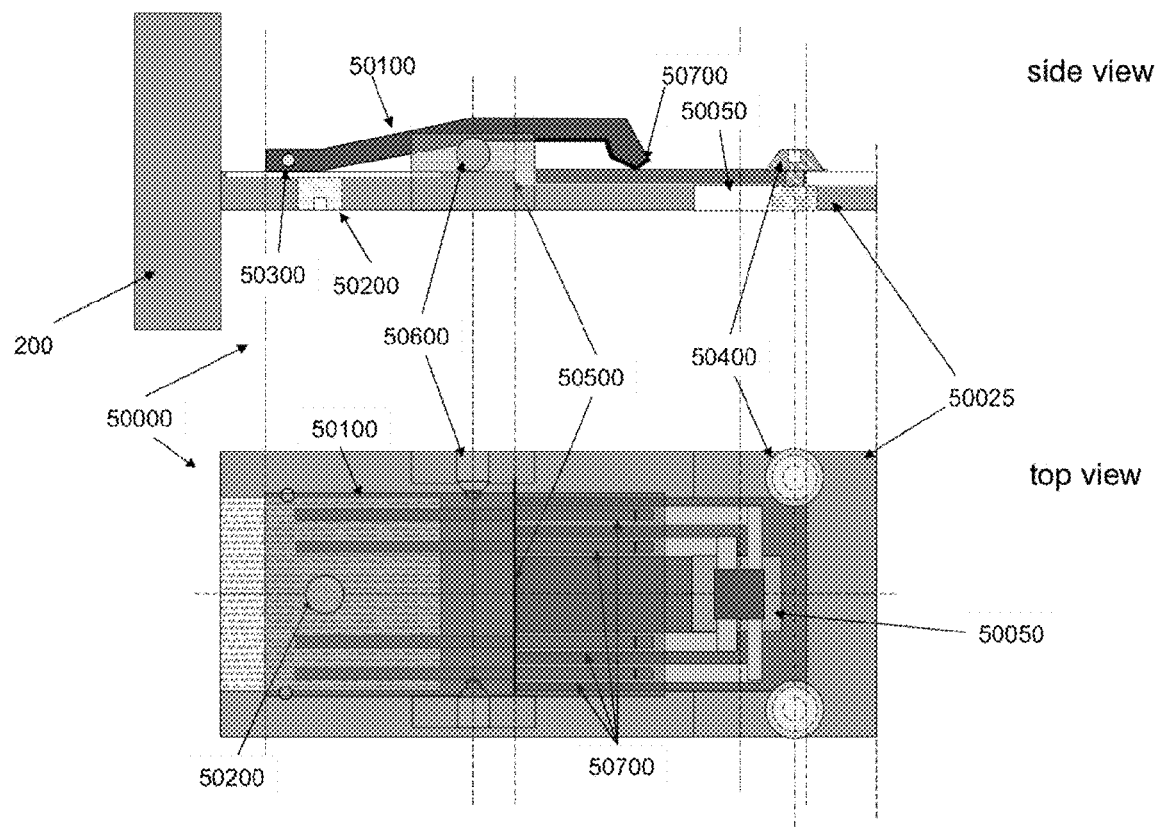
FIG. 4B shows a third embodiment of the tip region of a specimen holder described herein wherein the holder tip (50000) shows a flexing mechanism with a specimen support device, wherein the fulcrum is a two-piece fulcrum.
Figure 5A:
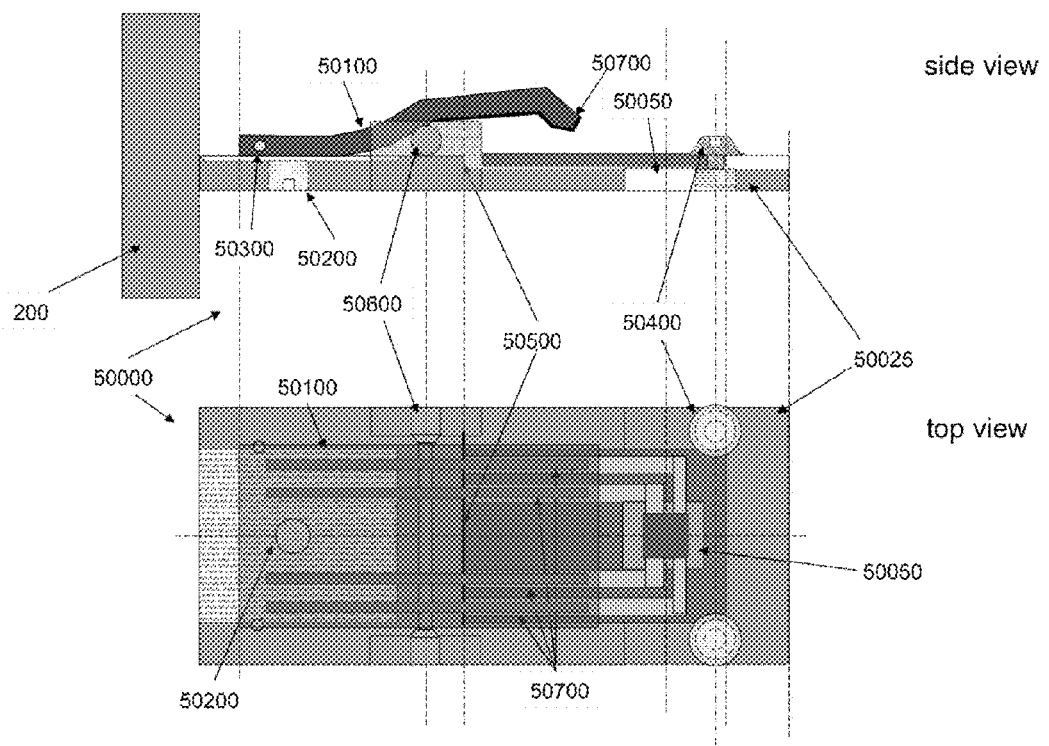
FIG. 5A shows a fourth embodiment of the tip region of a specimen holder described herein wherein the holder tip (50000) shows a flexing mechanism ready to receive a specimen support device, wherein the fulcrum is a one-piece fulcrum.
Figure 5B:
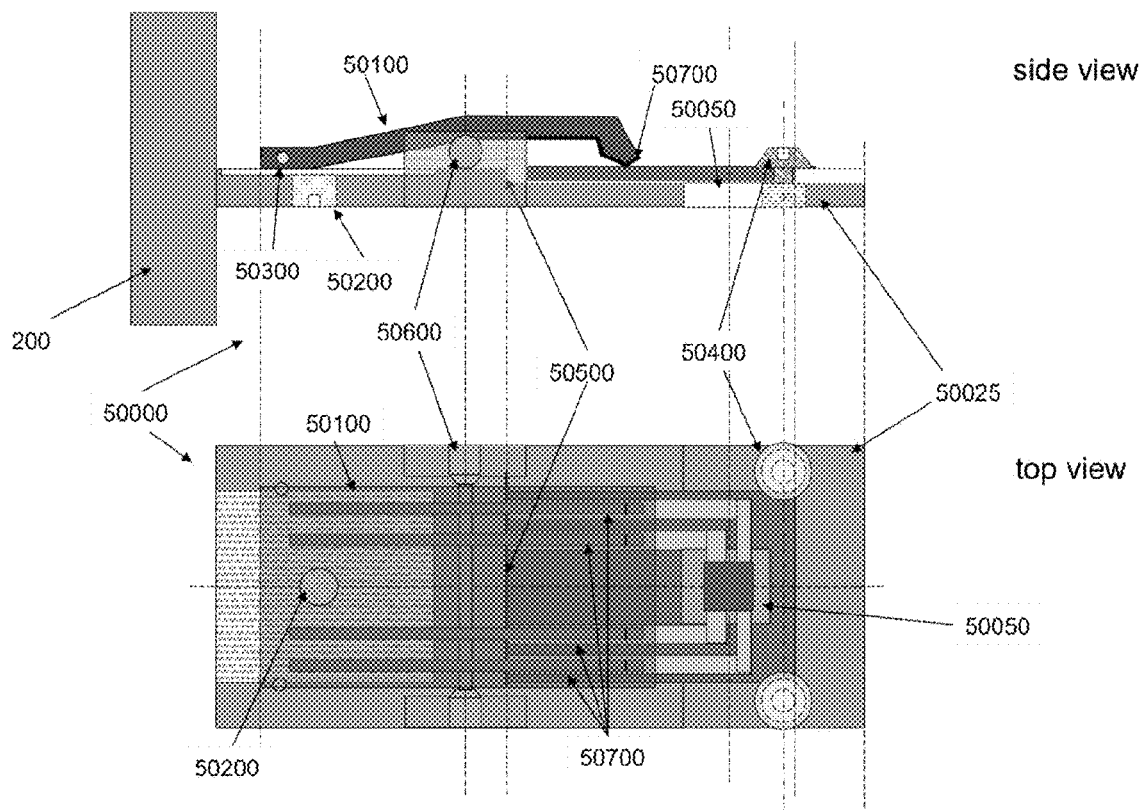
FIG. 5B shows a fourth embodiment of the tip region of a specimen holder described herein wherein the holder tip (50000) shows a flexing mechanism with a specimen support device, wherein the fulcrum is a one-piece fulcrum.

Yet another embodiment of the tip region of a specimen holder is shown in FIGS. 4A, 4B and 5A, 5B. FIGS. 4B and 5B show the tip region of a specimen holder of the present invention where the holder tip (50000) includes a flexible clamping mechanism in the resting state with a specimen support device loaded for use. FIGS. 4A and 5A show the tip region of the specimen holder of FIGS. 4B and 5B, respectively, where the holder tip (50000) is in a state ready for unloading a specimen support device. In all of these figures the flexible mechanism is comprised of a clip (50100) under which the device can be inserted, guide mechanism (50400), depth stop (50500), fulcrum (50600), fixed point (50300) and at least one electrical contact (50700). An optional set screw (50200) can be used to limit the distance that the clip can be flexed. The holder tip is comprised of a body (50025), a viewing region (50050) and a flexible clamping mechanism. The device is comprised of a frame (20000), electrical leads (20100), and a membrane region (20200). The difference between the 4A, 4B figures and the 5A, 5B figures is that in the former the fulcrum is a two-piece fulcrum and in the in latter the fulcrum is a one-piece fulcrum.

To mount the device under the clip (50100), the device is first oriented between the guide screws (50400) with the device's electrical leads (20100) oriented towards the slot. Downward pressure is then applied on the top surface of the clip (50100) at a point between the fulcrum (50600) and the fixed point (50300) resulting in the clip (50100) bending upward at the end near the guide mechanism (50400), such as guide screws, guide pins, or guide posts. With this pressure applied, the device is then inserted until the leading edge of the device meets the depth stop (50500). When the device is fully inserted against the depth stop (50500), the downward force on the clip (50100) is released which secures the device under the clip (50100) by friction during imaging and analysis. Simultaneous electrical contacts are formed between the electrical contacts (50700) underneath the clip (50100) and the electrical leads (20100) allowing electrical current to be passed from the electrical contacts (50700) to the electrical leads (20100). It should be appreciated by one skilled in the art that the electrical contacts of the specimen holder (50700) may extend from one length of the clip to the other or may be present in shorter sections so long as the electrical contacts are present for contact with the electrical leads of the device (20100).

Figure 6A:
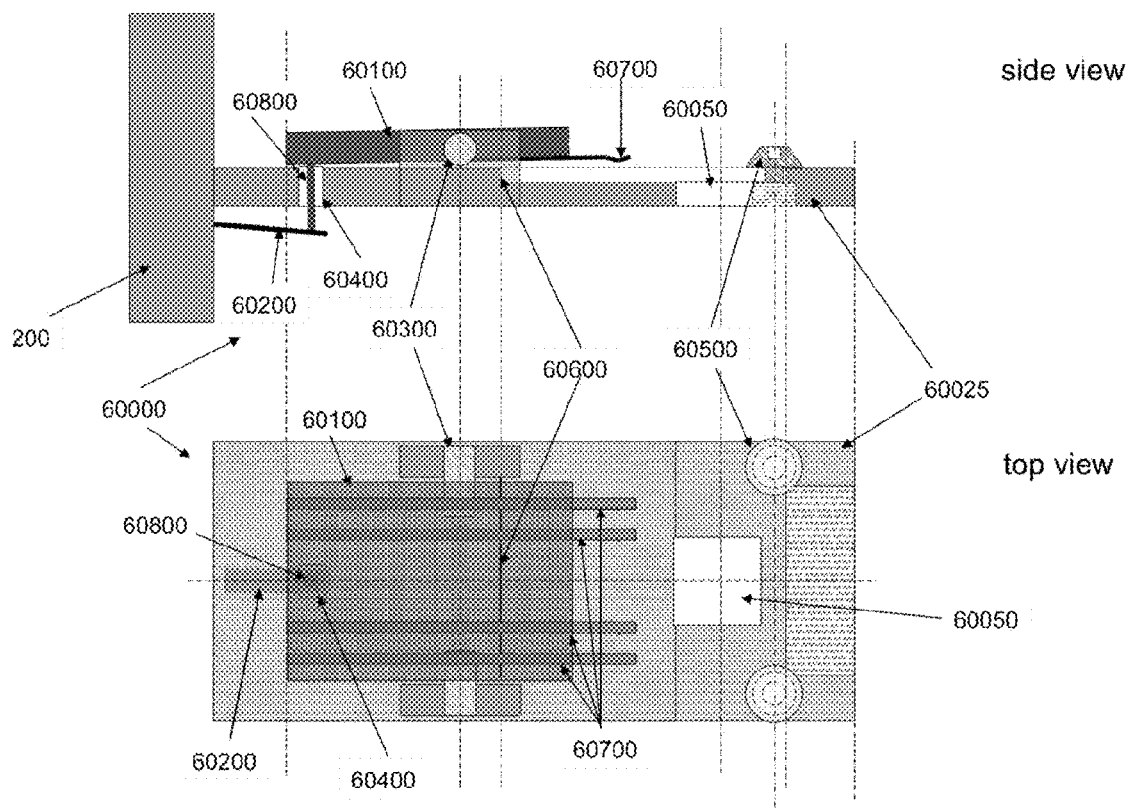
FIG. 6A shows a fifth embodiment of the tip region of a specimen holder described herein wherein the holder tip (60000) shows a clamping mechanism in an open state ready to receive a specimen support device.
Figure 6B:
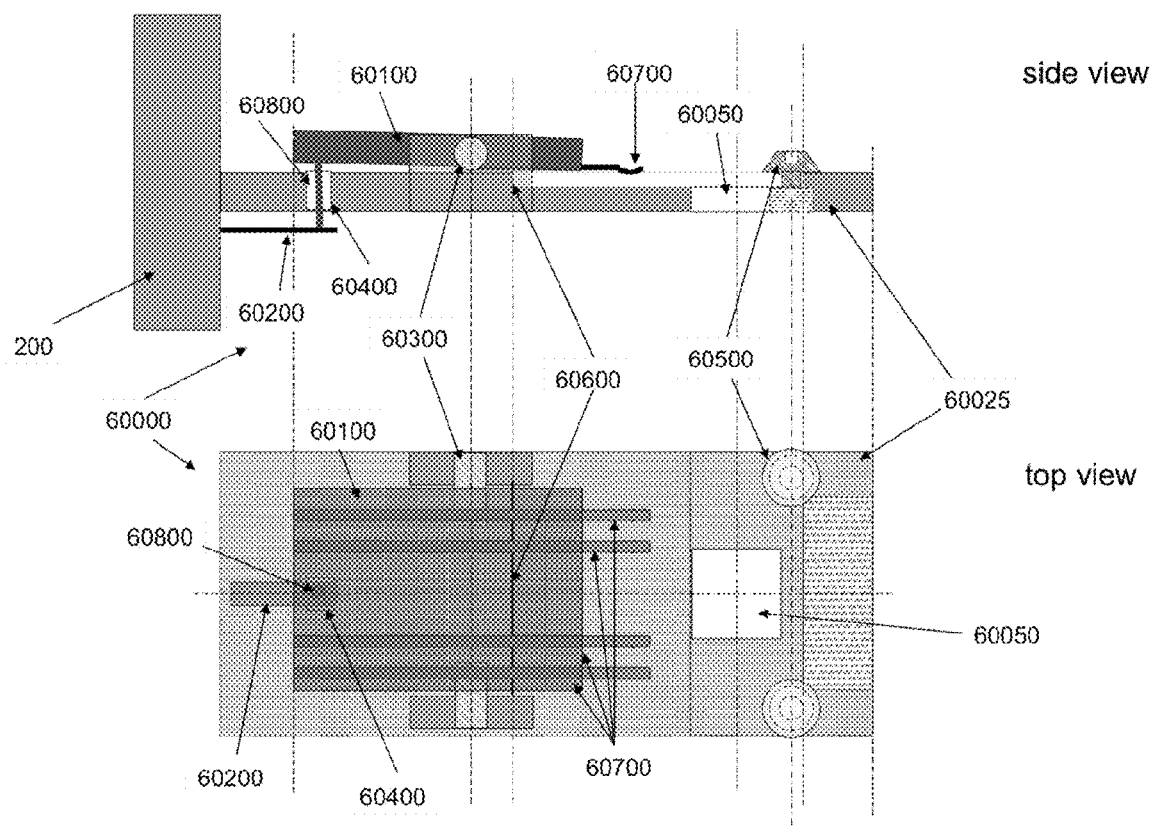
FIG. 6B shows a fifth embodiment of the tip region of a specimen holder described herein wherein the holder tip (60000) shows a clamping mechanism in a closed state without a specimen support device.
Figure 6C:
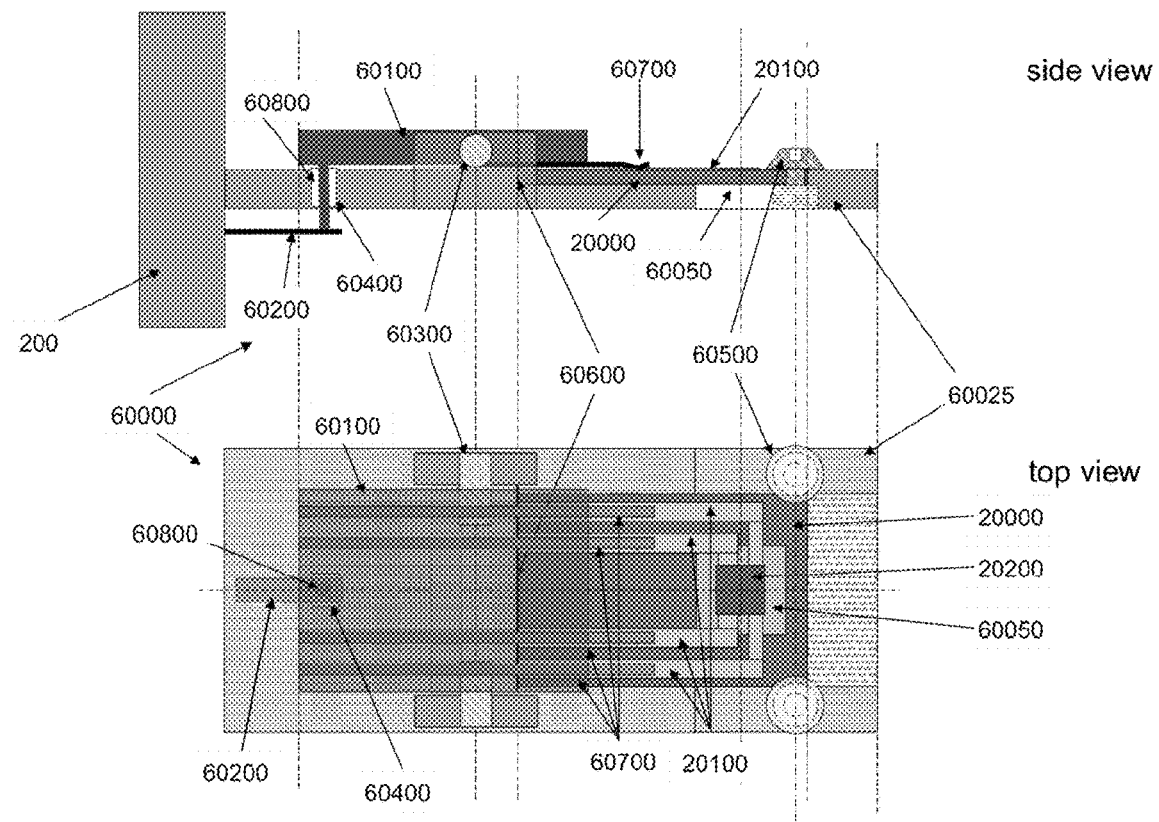
FIG. 6C shows a fifth embodiment of the tip region of a specimen holder described herein wherein the holder tip (60000) shows a clamping mechanism in a closed state with a specimen support device.

Another embodiment of the tip region of a specimen holder is shown in FIGS. 6A, 6B, and 6C. FIG. 6A shows the tip region of a specimen holder of the present invention where the holder tip (60000) includes a clamping mechanism in an open state ready to receive a specimen support device. FIG. 6B shows the tip region of the specimen holder of FIG. 6A where the holder tip (60000) is in a closed state without a specimen support device. FIG. 6C shows the tip region of the specimen holder of FIG. 6A where the holder tip (60000) is in a closed state with a specimen support device. In each of these figures, the clamping mechanism is comprised of a clip (60100), spring cantilever (60200), post (60800), post hole (60400), pivots (60300), guide mechanism (60500), depth stop (60600), and at least one electrical contact (60700). The post hole (60400) allows the post (60800) to contact and/or connect to both the spring cantilever (60200) and the clip (60100) through the holder tip (60000). The holder tip is comprised of a body (60025), a viewing region (60050), and the clamping mechanism. The electrical contact(s) preferably do not flex like a spring and will not be damaged from fatigue. In FIG. 6C a device is loaded into the tip and held in place by the clamping mechanism. The device is generally comprised of a frame (20000), electrical leads (20100), and a membrane region (20200).

In the clamping mechanism, the clip (60100) acts as a lever, the spring cantilever (60200) and post (60800) provide constant tension to the clip, the pivot (60300) allow the clip to pivot, and the guide mechanism (60500), such as guide screws, guide pins, or guide posts, provides lateral alignment to a device as it is loaded. When a device is completely loaded, the depth stop (60600) provides a means both to align the electrical contacts of the specimen holder (60700) to electrical leads of a device (20100) and to align the viewing region of the specimen holder tip (60050) with the membrane region of a device (20200). It should be appreciated by one skilled in the art that the electrical contacts of the specimen holder (60700) may extend from one length of the clip to the other or may be present in shorter sections so long as the electrical contacts are present for contact with the electrical leads of the device (20100). In addition the electrical contacts (60700) may consist of wires that protrude from the end of the clip, which make electrical contact to the electrical leads of the device (20100) using the bottom surface of the wire, or alternatively do not protrude from the end of the clip (see, e.g., FIG. 8 which illustrates the electrical contacts stopping at (or before) the end of the clip (60100).

The resting position for the clamping mechanism is shown in FIG. 6B where a spring cantilever (60200) pushes upward on a post (60800) through a post hole (60400), which pushes upward at one end of the clip (60100)), resulting in downward pressure created at the opposite end of the clip where the clip pivots at a set of pivots (60300) which may be smooth or threaded. The pivot is mounted to a mounting surface that is part of the body holder tip (60200).

To mount the device, downward pressure is placed on the spring end of the clip, which lifts the opposite end above the surface to a level at least as high as the thickness of the device, and typically higher, for example, greater than 1 mm (see FIG. 6A), although less than 1 mm is contemplated. The device is either placed in between the clip and the mounting surface manually, or slid underneath the clip along the mounting surface using the guide mechanism and depth stop as guidance. Once the device is in position, the pressure on the spring is released and the device is secured manually to the specimen tip (see FIG. 6C).

Electrical contacts from the holder to the device, typically in a range from 2 to 12 electrical contacts (60700 and 20100), may be provided by the conducting wires or paths and these electrical contacts may be positioned above, within, underneath and/or extended from the clip. These electrical contacts are electrically isolated from each other and from the clip itself (if the clip is made of a conductive material). When electrical pads exist on the device, the guide mechanism and depth stop will align the device with the clip to allow the electrical contacts from the clip and the pads from the device to contact one another when downward pressure on the clip is released. This will allow both mechanical pressure and electrical connections to be made in a novel, easy to operate design. The electrical contacts will be routed from the clip to the barrel, down the barrel to the end, and to a connector that exists at the specimen holder end that can be mated with a plug outside the microscope and connected to a power supply to provide voltage or current through the holder and interface to the specimen support device. Each conductor can remain isolated from each other as well as the three components that comprise the specimen holder.

Figure 7:
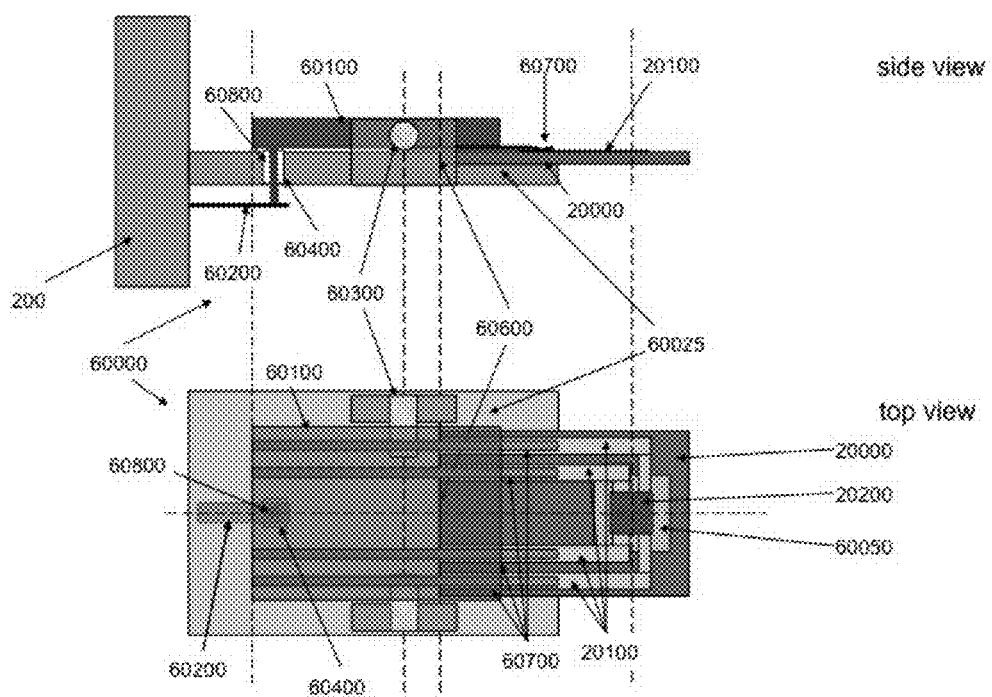
FIG. 7 shows an sixth embodiment of the tip region of a specimen holder described herein, wherein the holder tip (60000) shows a clamping mechanism in a closed state with a specimen support device.
Figure 8:
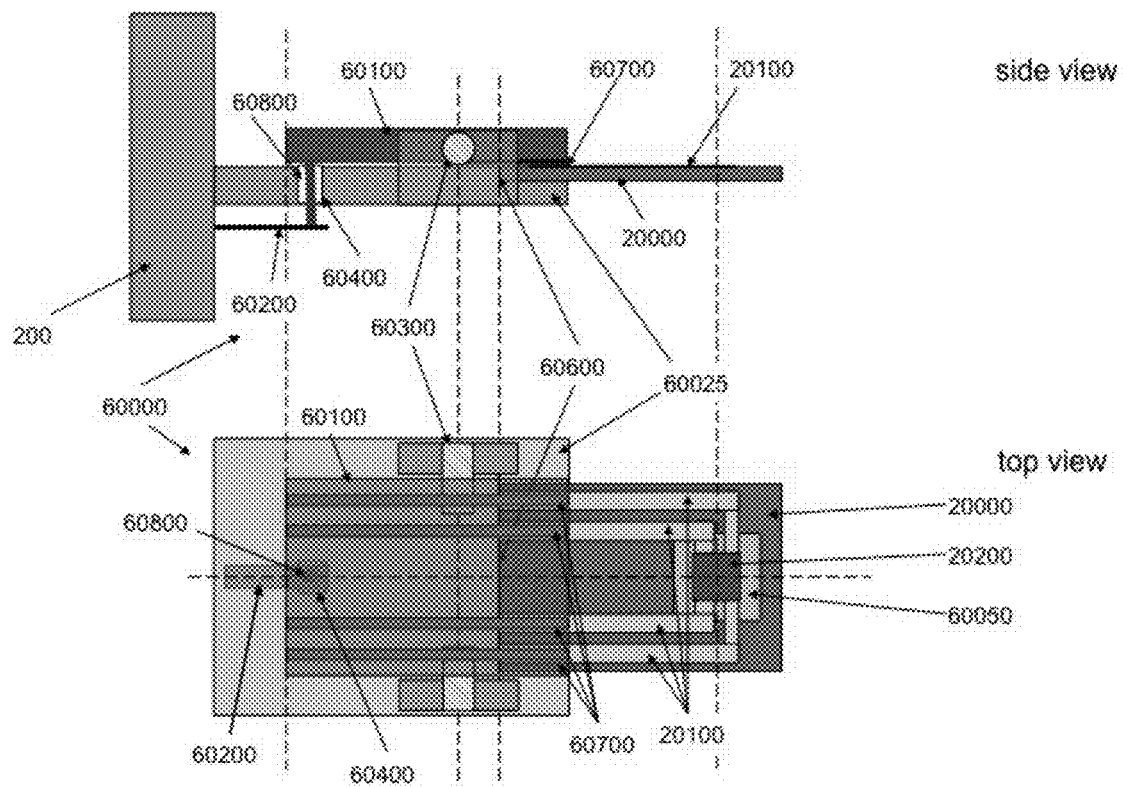
FIG. 8 shows an seventh embodiment of the tip region of a specimen holder described herein, wherein the holder tip (60000) shows a clamping mechanism in a closed state with a specimen support device.

Further embodiments of the tip region of the specimen holder are shown in FIGS. 7 and 8. FIG. 7 shows the tip region of a specimen holder similar to FIG. 6C, wherein the holder tip (60000) is in a closed state with a specimen support device, however, the mounting surface of the holder tip only extends about as far as the electrical contacts (60700) and as such, the holder tip does not include the viewing region of FIG. 6C. FIG. 8 also shows the tip region of a specimen holder similar to FIG. 6C, however, the electrical contacts do not extend beyond the end of the clip. Specifically, in FIGS. 7 and 8, the clamping mechanism is comprised of a clip (60100), spring cantilever (60200), post (60800), post hole (60400), pivots (60300), depth stop (60600), and at least one electrical contact (60700). The post hole (60400) allows the post (60800) to contact and/or connect to both the spring cantilever (60200) and the clip (60100) through the holder tip (60000). The electrical contact(s) preferably do not flex like a spring and will not be damaged from fatigue. The holder tip is comprised of a body (60025) and the clamping mechanism. In FIG. 7, the body (60025) extends just to the edge of the electrical contacts (60700) and the specimen support device (20000) cantilevers beyond the body (60025). In FIG. 8, the electrical contacts (60700) do not extend beyond the end of the clip (60100) and the body (60025) is illustrated to extend as far as the edge of the clip (60100), wherein the specimen support device (20000) cantilevers beyond the body (60025). The embodiments in FIGS. 7 and 8 allow a rigid specimen support to extend beyond the body (60025) and still maintain mechanical contact with the body (60025) and electrical contact with the clip (60100) through the electrical contacts (60700).

FIG. 7 and FIG. 8 are based upon the embodiment illustrated in FIGS. 6A, 6B and 6C, but may also be applied to the embodiments shown in FIGS. 2A, 2B, 2C, 3A, 3B, 3C, 4A, 4B, 5A and 5B, whereby the mounting surface of the holder tip only extends about as far as the electrical contacts and as such, the holder tip does not include the viewing region.

The advantages of the specimen holder described herein include, but are not limited to: the ready adaptation of the specimen holder to accommodate specimen support devices having varying shapes and sizes without the need to machine frames and custom parts to align different device geometries; providing a simple method for mounting and exchanging devices and making electrical contacts to devices without the need for partially disassembling the specimen tip; allowing for interchangeable specimen tips to accommodate different specimen supports or to be used with different barrels and ends; and eliminating the use of a delicate spring contact finger. For example, the electrical contacts of the present invention may be effectuated at one of the clip (see, e.g., FIGS. 2-8) whereby there is no spring present at all or the spring is distally positioned at the other end of the clip.

Although the invention has been variously disclosed herein with reference to illustrative embodiments and features, it will be appreciated that the embodiments and features described hereinabove are not intended to limit the invention, and that other variations, modifications and other embodiments will suggest themselves to those of ordinary skill in the art, based on the disclosure herein. The invention therefore is to be broadly construed, as encompassing all such variations, modifications and alternative embodiments within the spirit and scope of the claims hereafter set forth.

What is claimed is:

1. An electron microscope specimen holder comprising a body, a clipping means, and an interchangeable specimen support device, wherein the clipping means comprise an article of manufacture having a top surface, a bottom surface, a first end, a securing means, a second end, and at least one electrical contact integrated on and/or in the bottom surface of the article, wherein the interchangeable specimen support device is mechanically secured between the bottom surface of the clipping means and the body, and wherein the interchangeable specimen support device is selected from the group consisting of a window device and a temperature control device.

2. The electron microscope specimen holder of claim 1, wherein the electron microscope specimen holder further comprises at least one guide mechanism wherein the interchangeable specimen support device is aligned in the body by the at least one guide mechanism.

3. The electron microscope specimen holder of claim 1, wherein the interchangeable specimen support device comprises a temperature control device.

4. The electron microscope specimen holder of claim 3, wherein the temperature control device is used to control the temperature around a specimen positioned on the interchangeable specimen support device.

5. The electron microscope specimen holder of claim 3, wherein the temperature control device comprises:
   (a) a membrane comprising at least one membrane observation region, said membrane having a top side and a bottom side;
   (b) at least two conductive heat source elements in contact with the top side of the membrane, wherein the at least two heat source elements flank the at least one membrane observation region,
   wherein the membrane observation region is heatable, and wherein the membrane and the at least two heat source elements are both conductive, ceramic materials.

6. The electron microscope specimen holder of claim 5, wherein the at least two heat source elements are relatively more conductive than the membrane.

7. The electron microscope specimen holder of claim 5, wherein the at least two heat source elements are arranged so that current can be forced through the membrane thus allowing Joule heating to occur in the membrane observation region.

8. The electron microscope specimen holder of claim 5, wherein both the membrane and the at least two heat source elements are silicon carbide and have different conductivities.

9. The electron microscope specimen holder of claim 1, wherein the interchangeable specimen support device is mechanically secured between the clipping means and the body without disassembly of or soldering of the specimen holder.

10. The electron microscope specimen holder of claim 1, wherein an electrical contact to the specimen support device is provided once the specimen support device is mechanically secured and aligned.

11. The electron microscope specimen holder of claim 9, wherein disassembly comprises removing screws or other small parts.

12. The electron microscope specimen holder of claim 1, wherein the securing means comprise a pivot positioned between the first end and the second end of the article, wherein the second end of the article is pivotally raised by depressing the top surface of the first end of the article for insertion of the interchangeable specimen support device between the bottom surface of the second end of the article and a top surface of the body, and wherein the article is pivotally lowered such that the interchangeable specimen support device is mechanically secured.

13. The electron microscope specimen holder of claim 12, wherein at least one electrical lead of the interchangeable specimen support device substantially contacts at least one electrical contact of the article.

14. The electron microscope specimen holder of claim 1, wherein the securing means comprise a locking screw, wherein the interchangeable specimen support device is inserted between the bottom surface of the second end of the article and a top surface of the body by turning the locking screw in a direction such that the article is raised relative to the body, and wherein the article is lowered by turning the locking screw in the opposite direction such that the interchangeable specimen support device is mechanically secured.

15. The electron microscope specimen holder of claim 14, wherein at least one electrical lead of the interchangeable specimen support device substantially contacts at least one electrical contact of the article.

16. A method of repeatedly mounting and exchanging interchangeable specimen support devices in an electron microscope specimen holder, wherein said electron microscope specimen holder comprises a body, a clipping means, and the specimen support device, wherein the clipping means comprise an article of manufacture having a top surface, a bottom surface, a first end, a securing means, a second end, and at least one electrical contact integrated on and/or in the bottom surface of the article, and wherein the interchangeable specimen support device is selected from the group consisting of a window device and a temperature control device, said method comprising:
   inserting and mechanically securing the specimen support device between the bottom surface of the clipping means and the body without disassembly of or soldering of the specimen holder.

17. The method of claim 16, wherein the electron microscope specimen holder further comprises at least one guide mechanism, wherein the at least one guide mechanism permits the insertion and alignment of the interchangeable specimen support device in the body of the specimen holder.

18. The method of claim 16, wherein the interchangeable specimen support device comprises a temperature control device.

19. The electron microscope specimen holder of claim 17, wherein the temperature control device is used to control the temperature around a specimen positioned on the specimen control device.

* * * * *